(12) United States Patent
Huang et al.

(10) Patent No.: US 10,918,741 B2
(45) Date of Patent: *Feb. 16, 2021

(54) PSMA-TARGETING IMAGING AGENTS

(71) Applicant: THE CLEVELAND CLINIC FOUNDATION, Cleveland, OH (US)

(72) Inventors: Steve Shih-Lin Huang, Cleveland, OH (US); Warren D. Heston, Cleveland, OH (US); Xinning Wang, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/632,527

(22) Filed: Jun. 26, 2017

(65) Prior Publication Data
US 2017/0354748 A1 Dec. 14, 2017

Related U.S. Application Data

(63) Continuation of application No. 14/605,124, filed on Jan. 26, 2015, now Pat. No. 9,713,649.

(60) Provisional application No. 61/931,112, filed on Jan. 24, 2014.

(51) Int. Cl.
*A61K 51/04* (2006.01)
*A61K 49/00* (2006.01)

(52) U.S. Cl.
CPC ...... *A61K 49/0032* (2013.01); *A61K 49/0052* (2013.01); *A61K 51/0402* (2013.01); *A61K 51/0406* (2013.01); *A61K 51/0497* (2013.01)

(58) Field of Classification Search
None
See application file for complete search history.

(56) References Cited

U.S. PATENT DOCUMENTS

| | | | |
|---|---|---|---|
| 9,226,981 B2 | 1/2016 | Pomper et al. | |
| 9,371,362 B2 | 6/2016 | Ho | |
| 9,713,649 B2 | 7/2017 | Huang et al. | |
| 9,889,199 B2 * | 2/2018 | Basilion | A61K 9/0019 |
| 10,363,313 B2 * | 7/2019 | Basilion | A61K 47/64 |
| 10,434,194 B2 * | 10/2019 | Basilion | A61B 8/481 |
| 2007/0148662 A1 | 6/2007 | Israeli et al. | |
| 2013/0035583 A1 | 2/2013 | Park et al. | |
| 2013/0164220 A1 * | 6/2013 | Yu | A61K 49/0056 424/9.6 |
| 2013/0211420 A1 | 8/2013 | Jensen | |

OTHER PUBLICATIONS

Afshar-Oromieh, A. et al., "PET imaging with a [68Ga] gallium-labelled PSMA ligand for the diagnosis of prostate cancer: biodistribution in humans and first evaluation of tumour lesions." European journal of nuclear medicine and molecular imaging 40 (2013): 486-495.

Banerjee et al., "Synthesis and evaluation of technetium-99m-and rhenium-labeled inhibitors of the prostate-specific membrane antigen (PSMA)." Journal of medicinal chemistry 51.15 (2008): 4504-4517.

Banerjee et al., "68Ga-labeled inhibitors of prostate-specific membrane antigen (PSMA) for imaging prostate cancer." Journal of medicinal chemistry 53.14 (2010): 5333-5341.

Barinka, C. et al., "Interactions between Human Glutamate Carboxypeptidase II and Urea-Based Inhibitors: Structural Characterizationt." Journal of medicinal chemistry 51 (2008): 7737-7743.

Barrett, J. A. et al., "First-in-man evaluation of 2 high-affinity PSMA-avid small molecules for imaging prostate cancer." Journal of Nuclear Medicine 54.3 (2013): 380-387.

Chang, S.et al., "Five different anti-prostate-specific membrane antigen (PSMA) antibodies confirm PSMA expression in tumor-associated neovasculature." Cancer research 59.13 (1999): 3192-3198.

Chen, Y. et al., "2-(3-{1-Carboxy-5-[(6-[18F] fluoro-pyridine-3-carbonyl)-amino]-pentyl}-ureido)-pentanedioic acid, [18F] DCFPyL, a PSMA-based PET imaging agent for prostate cancer." Clinical Cancer Research 17.24 (2011): 7645-7653.

Chen, Y. et al., "A low molecular weight PSMA-based fluorescent imaging agent for cancer." Biochemical and biophysical research communications 390.3 (2009): 624-629.

Cramer, H. et al., "2-5A ligands—A new concept for the treatment of prostate cancer." Nucleosides, Nucleotides, and Nucleic Acids 26.10-12 (2007): 1471-1477.

Difilippo, F., "Design and performance of a multi-pinhole collimation device for small animal imaging with clinical SPECT and SPECT-CT scanners." Physics in medicine and biology 53.15 (2008): 4185-4201.

(Continued)

*Primary Examiner* — Katherine Peebles
(74) *Attorney, Agent, or Firm* — Pearne & Gordon LLP

(57) ABSTRACT

A PSMA-specific imaging agent comprising a compound according to formula I:

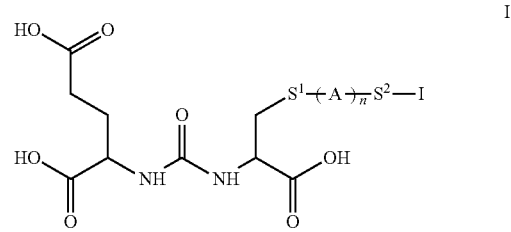

are described, wherein $S^1$ is an organic spacer group having from 5 to 30 carbons, A is an amino acid forming a portion of a negatively charged peptide oligomer, n is from 3 to 6, $S^2$ is an organic spacer group having from 5 to 15 carbons, and I is an imaging group, and pharmaceutically acceptable salts thereof. The PSMA-specific imaging agents can be used to image PSMA within a tissue region to guide the treatment of diseases such as prostate cancer.

8 Claims, 5 Drawing Sheets
Specification includes a Sequence Listing.

(56) References Cited

OTHER PUBLICATIONS

Eiffler et al., "A fluorescent imaging agent specifically targeted prostate specific membrane antigen-expressing cells", The Journal of Urology, vol. 185, No. 43, Supplement, Tuesday May 17, 2011.
Gordetsky et al., "Indocyanine green (ICG): a novel approach to pelvic lymph node identification in radical cystectomy specimens", The Journal of Urology, vol. 185, No. 4S, Supplement, Monday May 16, 2011.
Haubner, R. et al., "Glycosylated RGD-containing peptides: tracer for tumor targeting and angiogenesis imaging with improved biokinetics," Journal of Nuclear Medicine 42.2 (2001): 326-336.
Hillier, S. M. et al., "Preclinical evaluation of novel glutamate-urealysine analogs that target prostate-specific membrane antigen as molecular imaging pharmaceuticals for prostate cancer." Cancer research 69.17 (2009): 6932-6940.
Huang, S. et al., "Improving the biodistribution of PSMA-targeting tracers with a highly negatively charged linker." The Prostate 74.7 (2014): 702-713.
Kovar, J. L. et al., "A systematic approach to the development of fluorescent contrast agents for optical imaging of mouse cancer models." Analytical biochemistry 367.1 (2007): 1-12.
Kozikowski, A. P. et al., "Design of remarkably simple, yet potent urea-based inhibitors of glutamate carboxypeptidase II (NAALADase)." Journal of medicinal chemistry 44.3 (2001): 298-301.
Kularatne, S. A. et al., "Design, synthesis, and preclinical evaluation of prostate-specific membrane antigen targeted 99mTc-radioimaging agents," Molecular pharmaceutics 6.3 (2009): 790-800.
Laverman, P. et al., "Optimized labeling of NOTA-conjugated octreotide with F-18." Tumor Biology 33.2 (2012): 427-434.
Laydner, H., et al., "Robotic real-time near infrared targeted fluorescence imaging in a murine model of prostate cancer: a feasibility study," Urology 81.2 (2013): 451-457.
Liu, T.et al., "A targeted low molecular weight near-infrared fluorescent probe for prostate cancer." Bioorganic & medicinal chemistry letters 20.23 (2010): 7124-7126.
McBride, W. J. et al., "A novel method of 18F radiolabeling for PET." Journal of nuclear medicine 50.6 (2009): 991-998.
Mesters, J.et al., "Structure of glutamate carboxypeptidase II, a drug target in neuronal damage and prostate cancer," The EMBO journal25.6 (2006): 1375-1384.
Molecular Imaging and Contrast Agent Database (MICAD), Bethesda (MD): National Center for Biotechnology Information (US); 2004-2013, pp. 1-6.
Nakajima, T. et al., "Targeted, activatable, in vivo fluorescence imaging of prostate-specific membrane antigen (PSMA) positive tumors using the quenched humanized J591 antibody-indocyanine green (ICG) conjugate." Bioconjugate chemistry 22.8 (2011): 1700-1705.
Pohle, K. et al., "68 Ga-NODAGA-RGD is a suitable substitute for 18 F-Galacto-RGD and can be produced with high specific activity in a cGMP/GRP compliant automated process." Nuclear medicine and biology 39.6 (2012): 777-784.
Reske, S. N. et al., "Comment on Afshar-Oromieh et al.: PET imaging with a [68Ga] gallium-labelled PSMA ligand for the diagnosis of prostate cancer: biodistribution in humans and first evaluation of tumour lesions." European journal of nuclear medicine and molecular imaging 40.6 (2013): 969-970.
Tobis, S. et al., "Near infrared fluorescence imaging with robotic assisted laparoscopic partial nephrectomy: initial clinical experience for renal cortical tumors." The Journal of urology 186.1 (2011): 47-52.
Tolmachev, V. et al., "HEHEHE-tagged affibody molecule may be purified by IMAC, is conveniently labeled with [99mTc (CO) 3]+, and shows improved biodistribution with reduced hepatic radioactivity accumulation," Bioconjugate chemistry 21.11 (2010): 2013-2022.
Vanderpoel, H. G. et al., "Intraoperative laparoscopic fluorescence guidance to the sentinel lymph node in prostate cancer patients: clinical proof of concept of an integrated functional imaging approach using a multimodal tracer." European urology 60.4 (2011): 826-833.
Wang, X. et al., "Structure-Activity Relationships of 2', 5'-0iigoadenylate Analogue Modifications of Prostate-Specific Membrane Antigen (PSMA) Antagonists." Nucleosides, Nucleotides and Nucleic Acids 31.5 (2012): 432-444.
Wang, X. et al., "Development of Targeted Near-Infrared Imaging Agents for Prostate Cancer." Molecular cancer therapeutics 13.11 (2014): 2595-2606.
Zhang, A. X. et al., "A remote arene-binding site on prostate specific membrane antigen revealed by antibody-recruiting small molecules." Journal of the American Chemical Society 132.36 (2010): 12711-12716.
Cho, S. Y., et al., "Biodistribution, Tumor Detection, and Radiation Dosimetry of 18F-DCFBC, A Low-Molecular-Weight Inhibitor of Prostate-Specific Membrane Antigen, in Patients with Metastatic Prostate Cancer." Journal of Nuclear Medicine 53. 12 (2012): 1883-1891.

* cited by examiner

SEQUENCE LISTING

```
<160> NUMBER OF SEQ ID NOS: 24

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term ZJ-MCC
<220> FEATURE:
<221> NAME/KEY: MOD_RES
<222> LOCATION: (1)..(1)
<223> OTHER INFORMATION: Ahx

<400> SEQUENCE: 1

Xaa Glu Glu Glu Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term ZJ-MCC
<220> FEATURE:
<221> NAME/KEY: MOD_RES
<222> LOCATION: (1)..(1)
<223> OTHER INFORMATION: Ahx

<400> SEQUENCE: 2

Xaa Tyr Tyr Tyr Gly
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term Amc conjugated to
      OtBu-Glu(OtBu)-NH-CO-NH-Glu-OtBu
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (2)..(4)
<223> OTHER INFORMATION: D-Glu

<400> SEQUENCE: 3

Xaa Xaa Xaa Xaa Gly Tyr Gly Gly Gly Cys
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Amc conjugated to
      OtBu-Glu(OtBu)-NH-CO-NH-Glu-OtBu
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (6)..(6)
<223> OTHER INFORMATION: Lys(Bn-NOTA)

<400> SEQUENCE: 4

Xaa Glu Glu Glu Tyr Lys
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term conjugated to
      OtBu-Glu(OtBu)-NH-CO-NH-Glu-OtBu via urea bond
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (6)..(6)
<223> OTHER INFORMATION: Lys(Bn-NOTA)

<400> SEQUENCE: 5

Xaa Glu Glu Glu Tyr Lys
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term ZJ-MCC
<220> FEATURE:
<221> NAME/KEY: MOD_RES
<222> LOCATION: (1)..(3)
```

```
<223> OTHER INFORMATION: D-Glu
<220> FEATURE:
<221> NAME/KEY: MOD_RES
<222> LOCATION: (5)..(5)
<223> OTHER INFORMATION: Lys(IRDye800cw)

<400> SEQUENCE: 6

Xaa Xaa Xaa Gly Lys Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Amc conjugated to
      OtBu-Glu(OtBu)-NH-CO-NH-Glu-OtBu
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (2)..(4)
<223> OTHER INFORMATION: D-Glu
<220> FEATURE:
<223> OTHER INFORMATION: C-term NH2

<400> SEQUENCE: 7

Xaa Xaa Xaa Xaa Gly Tyr Gly Gly Gly Cys
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Amc conjugated to
      OtBu-Glu(OtBu)-NH-CO-NH-Glu-OtBu
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (2)..(4)
<223> OTHER INFORMATION: D-Glu
<220> FEATURE:
<221> NAME/KEY: MOD_RES
<222> LOCATION: (6)..(6)
<223> OTHER INFORMATION: Lys(Bn-NOTA)
<220> FEATURE:
<223> OTHER INFORMATION: C-term NH2

<400> SEQUENCE: 8

Xaa Xaa Xaa Xaa Tyr Lys
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term conjugated to
```

```
        OtBu-Glu(OtBu)-NH-CO-NH-Glu-OtBu via urea bond
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (6)..(6)
<223> OTHER INFORMATION: Lys(Bn-NOTA)
<220> FEATURE:
<223> OTHER INFORMATION: C-term NH2

<400> SEQUENCE: 9

Xaa Glu Glu Glu Tyr Lys
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term ZJ-MCC
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (2)..(4)
<223> OTHER INFORMATION: D-Glu

<400> SEQUENCE: 10

Xaa Xaa Xaa Xaa Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Fmoc
<220> FEATURE:
<221> NAME/KEY: MOD_RES
<222> LOCATION: (1)..(1)
<223> OTHER INFORMATION: Ahx

<400> SEQUENCE: 11

Xaa Tyr Tyr Tyr Gly
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Amc conjugated to Fmoc-Glu-OtBu
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (2)..(4)
<223> OTHER INFORMATION: D-Glu
```

```
<220> FEATURE:
<223> OTHER INFORMATION: C-term NH2

<400> SEQUENCE: 12

Xaa Xaa Xaa Xaa Gly Tyr Gly Gly Gly Cys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Amc conjugated to Glu(OtBu)
<220> FEATURE:
<221> NAME/KEY: MOD_RES
<222> LOCATION: (1)..(1)
<223> OTHER INFORMATION: Ahx
<220> FEATURE:
<223> OTHER INFORMATION: C-term NH2

<400> SEQUENCE: 13

Xaa Glu Glu Glu Gly Tyr Gly Gly Gly Cys
1               5                   10

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Amc conjugated to Fmoc-Glu-OtBu
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (2)..(4)
<223> OTHER INFORMATION: D-Glu
<220> FEATURE:
<223> OTHER INFORMATION: C-term NH2

<400> SEQUENCE: 14

Xaa Xaa Xaa Xaa Tyr Lys
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Amc conjugated to
      OtBu-Glu(OtBu)-NH-CO-NH-Glu-OtBu
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (6)..(6)
<223> OTHER INFORMATION: Lys(Bn-NOTA)
<220> FEATURE:
<223> OTHER INFORMATION: C-term NH2

<400> SEQUENCE: 15
```

```
Xaa Glu Glu Glu Tyr Lys
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Amc conjugated to
      OtBu-Glu(OtBu)-NH-CO-NH-Glu-OtBu
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (2)..(4)
<223> OTHER INFORMATION: D-Glu

<400> SEQUENCE: 16

Xaa Xaa Xaa Xaa Tyr Lys
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term conjugated to Fmoc-Glu-OtBu
      via urea bond
<220> FEATURE:
<221> NAME/KEY: MOD_RES
<222> LOCATION: (1)..(1)
<223> OTHER INFORMATION: Ahx
<220> FEATURE:
<223> OTHER INFORMATION: C-term NH2

<400> SEQUENCE: 17

Xaa Glu Glu Glu Tyr Lys
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term conjugated to
      OtBu-Glu(OtBu)-NH-CO-NH-Glu-OtBu via urea bond
<220> FEATURE:
<221> NAME/KEY: MOD_RES
<222> LOCATION: (1)..(1)
<223> OTHER INFORMATION: Ahx

<400> SEQUENCE: 18

Xaa Glu Glu Glu Tyr Lys
1               5

<210> SEQ ID NO 19
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 19

Gly Gly Gly Cys
1

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Amc conjugated to
      OtBu-Glu(OtBu)-NH-CO-NH-Glu-OtBu -Tc(99m)
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (2)..(4)
<223> OTHER INFORMATION: D-Glu

<400> SEQUENCE: 20

Xaa Xaa Xaa Xaa Gly Tyr Gly Gly Gly Cys
1               5                   10

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Tyr Gly Gly Gly Cys
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Amc conjugated to
      OtBu-Glu(OtBu)-NH-CO-NH-Glu-OtBu
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (2)..(4)
<223> OTHER INFORMATION: D-Glu
<220> FEATURE:
<221> NAME/KEY: MOD_RES
<222> LOCATION: (6)..(6)
<223> OTHER INFORMATION: Lys(Bn-NOTA)

<400> SEQUENCE: 22

Xaa Xaa Xaa Xaa Tyr Lys
1               5

<210> SEQ ID NO 23
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Amc conjugated to
      OtBu-Glu(OtBu)-NH-CO-NH-Glu-OtBu -18F aluminum-fluoride
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (2)..(4)
<223> OTHER INFORMATION: D-Glu
<220> FEATURE:
<221> NAME/KEY: MOD_RES
<222> LOCATION: (6)..(6)
<223> OTHER INFORMATION: Lys(Bn-NOTA)

<400> SEQUENCE: 23

Xaa Xaa Xaa Xaa Tyr Lys
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: D-Glu

<400> SEQUENCE: 24

Xaa Xaa Xaa Gly Lys Gly
1               5
```

PSMA-TARGETING IMAGING AGENTS

CROSS-REFERENCES TO RELATED APPLICATION

This application is a continuation of U.S. patent application Ser. No. 14/605,124, filed Jan. 26, 2015, which claims the benefit of U.S. Provisional Patent Application 61/931,112 filed on Jan. 24, 2014, and entitled BIODISTRIBUTION OF PSMA-TARGETING TRACERS WITH A HIGHLY NEGATIVELY CHARGED LINKER, the entirety of which is incorporated by reference herein.

GOVERNMENT FUNDING

This invention was made with government support under Army Grant #W81XWH-10-1-0218, awarded by the U.S. Department of Defense. The government has certain rights in the invention

SEQUENCE LISTING

The instant application contains a Sequence Listing which has been submitted in ASCII format via EFS-Web and is hereby incorporated by reference in its entirety. Said ASCII copy, created on Sep. 24, 2019, is named CCF023110.txt and is 9,075 bytes in size.

BACKGROUND

Prostate cancer is the most common malignancy in males and the second leading cause of death from cancer in men. It is estimated that there will be 238,590 new cases of prostate cancer in 2013. The majority of these patients will undergo definitive treatment. However, about 35% are expected to have biochemical recurrence within 10 years. This translates to nearly 70,000 patients a year with PSA recurrence after definitive therapy. Currently, no commercially available molecular imaging agent can effectively localize regional prostate metastases in soft tissue. Talab et al., Radiol Clin North Am; 50(6):1015-1041 (2012). The development of a sensitive and specific method to non-invasively localize prostate cancer in its early stages within the prostate and in local pelvic lymph nodes would profoundly change the workup and management of prostate cancer.

Small molecule inhibitors of prostate specific membrane antigen (PSMA) have shown the potential to be good agents for prostate cancer imaging. PSMA is a type II membrane protein with a very short intracellular domain connected by a single transmembrane helix to a large extracellular domain. Israeli et al., Cancer Res; 53(2):227-230 (1993). PSMA was first identified as the molecular target of the 7E11-C5 antibody which selectively binds LNCaP cells. In addition to its normal expression in the central nervous system, urogenital system, and small bowel, PSMA is overexpressed on prostate cancer cells and tumor neovasculature. A simple, easy to synthesize, and yet potent, urea-based small molecule inhibitor of PSMA was first published in 2001. Kozikowski et al., J Med Chem; 44(3):298-301 (2001). During the last decade, the simple di-amino acid urea compounds first made by Kozikowski et al. have evolved into a myriad of imaging agents for single photon emission tomography (SPECT) and positron emission tomography (PET).

Small molecule PET and SPECT PSMA tracers that have been tested in animals and humans have demonstrated a great advancement compared to antibody-based SPECT imaging with $^{111}$In-capromab pendetide. $^{18}$F-DCFBC was the first PSMA-targeting PET tracer to be tested in humans. Cho et al., J Nucl Med; 53(12):1883-1891 (2013). In a small five-patient trial, $^{18}$F-DCFBC detected lymph node and bone metastases at 2 hr post injection. In a seven-patient phase 1 study of $^{123}$I-MIP-1072 and $^{123}$I-MIP-1095, the SPECT tracer also demonstrated detection of soft tissue and bone metastases, as well as tumors in the prostate bed. Barrett et al., J Nucl Med; 54(3):380-387 (2013). Afshar-Oromieh et al. tested Glu-NH—CO—NHLys(Ahx)-[$^{68}$Ga(HBED-CC)] in 37 patients with prostate cancer and demonstrated a (per patient) lesion detection rate of 60% at PSA <2.2 ng/ml and a detection rate of 100% at PSA >2.2 ng/ml. Afshar-Oromieh et al., Eur J Nucl Med Mol Imaging; 40(4):486-495 (2013). All of these early human trials showed good lesion to background contrast at a few hours post injection compared to $^{111}$In-capromab penditide images, which need to be acquired 4 days post injection. However, $^{18}$F-DCFBC also had elevated liver background and unexpected blood pool retention. $^{123}$I-MIP-1072, $^{123}$I-MIP-1095, and Glu-NH—CO—NH-Lys(Ahx)-[$^{68}$Ga(HBEDCC)] all showed significant uptake in salivary glands, lacrimal glands, and liver. These organs have no significant expression of PSMA. When the tracer molecules are used as diagnostic agents, the elevated background affects the overall sensitivity of detection. If these agents would be used for therapy, unintended background would increase the overall toxicity of the treatment.

The non-PSMA related background activity exhibited by the current tracers may be due to hydrophobic interactions. Small radiolabeled PSMA tracers contain an aromatic group for convenient radiohalogenation. Many of the imaging agents with bulky NIR fluorophores and radionuclide chelates have long slender hydrophobic linkers that join the fluorophor or metal chelate to the di-amino acid urea moiety. A long linker is necessary because a 20 Å substrate tunnel connects the surface of PSMA with its deep ectodomain. Mesters et al., EMBO J.; 25(6):1375-1384 (2006). Early design efforts with $^{99m}$Tc tracers demonstrated that there is a minimal linker length needed for proper binding. Banerjee et al., J. Med Chem; 51(15):4504-4517 (2008). In the available high resolution structures (such as PDB 3D7G and 3D7H), where space allows, only a few crystallographic water molecules are seen within the tunnel. Given the known structure of PSMA, one would expect low binding affinity for RBI-1033, a urea-based PSMA targeting compound containing a bulky 2-5 Å moiety in the substrate tunnel region. Cramer Nucleosides Nucleotides Nucleic Acids; 26(10-12):1471-1477 (2007). The axial dimension of the 2-5 Å moiety greatly exceeds the width of the tunnel.

Surprisingly, RBI1033 exhibits ten times higher affinity toward PSMA than its "parent" urea ligand. The high affinity of RBI-1033 and its derivatives to PSMA suggest that a bulky linker is acceptable in the substrate tunnel. Wang et al., Nucleosides Nucleotides Nucleic Acids; 31(5):432-444 (2012). However, there remains a need for additional compounds useful as PSMA imaging agents.

SUMMARY OF THE INVENTION

Through iterative redesign, a series of PSMA inhibitors were designed with highly negatively charged linkers that connect to urea inhibitors and bulky radionuclide chelates. In vivo imaging and biodistribution studies were then performed with the radiolabeled tracers. The tracers derived from the iterative redesign have affinities for PSMA comparable to the "parent" urea ligand Cys-C(O)-Glu. Using a fluorine-18 labeled PSMA targeting tracer, it was found that these highly negatively charged molecules exhibit rapid renal excretion with minimal non-specific binding. The biodistribution data at 2 hr showed 4.6% ID/g PC3-PIP tumor uptake with spleen, liver, bone, and blood background levels of 0.1%, 0.17%, 0.1%, and 0.04%, respectively.

Placement of multiple negative charges in the linker region of PSMA tracers significantly reduced the non-specific background binding without significant reduction of binding affinity. This increased tumor/background contrast in positron emission tomography promises to provide more sensitive tumor detection while decreasing the overall radiation exposure to patients.

DETAILED DESCRIPTION OF THE INVENTION

Figure 1:
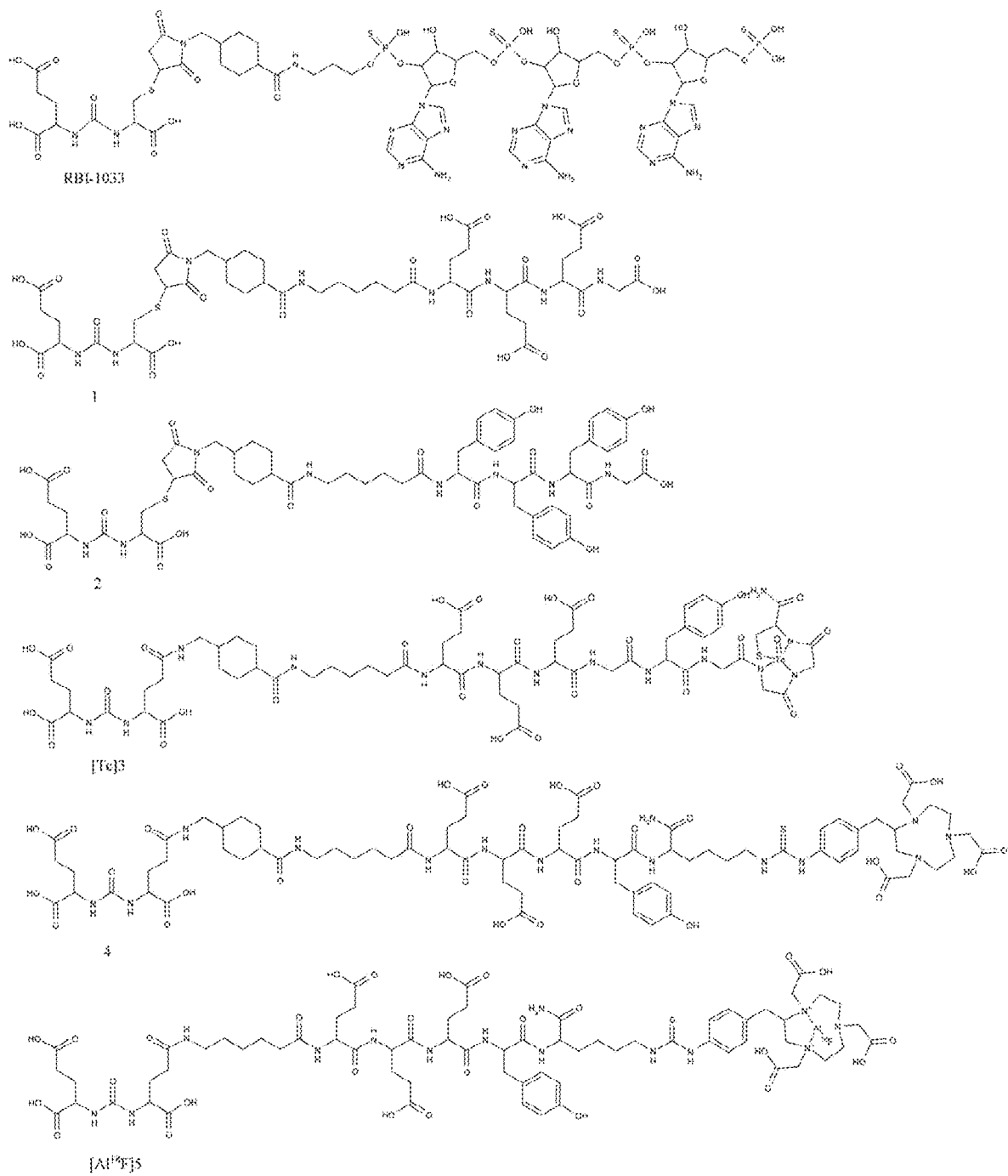
FIG. 1 provides a scheme showing the chemical structures of RBI-1033(Top), ZJ-MCC-Ahx-EEEG (compound 1) (SEQ ID NO: 1), ZJ-MCC-Ahx-YYYG (compound 2) (SEQ ID NO: 2), E'EAmc-Ahx-dEdEdEGYGGGC (SEQ ID NO: 3) in the presumed structure of the technetium bound form [$^{99m}$Tc]3, E'EAmc-Ahx-EEEYK(Bn-NOTA) (compound 4) (SEQ ID NO: 4) and the presumed structure of E'E-Ahx-EEEYK(Bn-NOTA) (SEQ ID NO: 5) with a bound aluminum-fluoride complex ([Al$^{18}$F] 5).

Through iterative re-design of RBI-1033, the inventors found that the linker region is amenable to further engineering and one can construct PSMA tracers with relatively bulky negatively charged linker regions. The inventors further demonstrated that such a negatively charged agent exhibits an improved biodistribution profile with a lower overall background compared to existing agents in the literature.

Definitions

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Image" or "imaging" refers to a procedure that produces a picture of an area of the body, for example, organs, bones, tissues, or blood.

"Pharmaceutically acceptable" as used herein means that the compound or composition is suitable for administration to a subject for the methods described herein, without unduly deleterious side effects.

As used herein, "a detectably effective amount" of the imaging agent of the invention is defined as an amount sufficient to yield an acceptable image using equipment which is available for clinical use. A detectably effective amount of the imaging agent of the invention may be administered in more than one injection. The detectably effective amount of the imaging agent of the invention can vary according to factors such as the degree of susceptibility of the individual, the age, sex, and weight of the individual, idiosyncratic responses of the individual, and the dosimetry. Detectably effective amounts of the imaging agent of the invention can also vary according to instrument and film-related factors. Optimization of such factors is well within the level of skill in the art. The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

The terms "comprising" and variations thereof do not have a limiting meaning where these terms appear in the description and claims.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for PSMA-specific imaging agents are those that do not interfere with the compounds activity. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

Cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

Unless otherwise indicated, the term "heteroatom" refers to the atoms O, S, or N.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The term "amino acid" as used herein is understood to mean an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Natural amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Other amino acids include, but not limited to, arginosuccinic acid, citrulline, cysteine sulfinic acid, 3,4-dihydroxyphenylalanine, homocysteine, homoserine, ornithine, carnitine, selenocysteine, selenomethionine, 3-monoiodotyrosine, 3,5-diiodotryosine, 3,5,5'-triiodothyronine, and 3,3',5,5'-tetraiodothyronine.

Compounds described herein can exist or be converted to a pharmaceutically acceptable salt. The salts can be prepared by treating the free acid with an appropriate amount of a chemically or pharmaceutically acceptable base. Representative chemically or pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. (e.g. at room temperature). The molar ratio of the compound to base used is chosen to provide the ratio desired for particular salts. For preparing, for example, the ammonium salts of the free acid starting material, the starting material can be treated with approximately one equivalent of base to yield a salt.

Certain compounds described herein may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Prostate specific membrane antigen (PSMA) is a type II membrane protein with a very short intracellular domain connected by a single transmembrane helix to a large extracellular domain. PSMA is overexpressed on most solid tumor neovasculature, as well as in prostate cancer, and is therefore a useful target for imaging agents. Chang et al., Cancer Res. 59, 3192-3198 (1999). For further information regarding the prostate specific membrane antigen, see US Patent Publication No. 2007/0148662, the disclosure of which is incorporated herein by reference.

PSMA-Specific Imaging Agents

In one aspect, the present invention provides PSMA-specific imaging agents, which are compounds according to formula I:

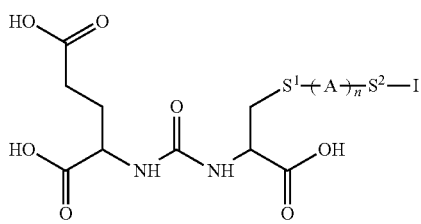

wherein $S^1$ is an organic spacer group having from 5 to 30 carbons, A is a negatively charged amino acid forming a portion of a peptide oligomer, n is from 3 to 6, $S^2$ is an organic spacer group having from 5 to 15 carbons, and I is an imaging group, and pharmaceutically acceptable salts thereof.

PSMA-specific, as used herein, refers to the fact that imaging agents specifically bind to PSMA rather than other biomaterial. As used herein, the term "specifically binding" refers to the interaction of the imaging agent with a second chemical species, wherein the interaction is dependent upon the presence of a particular structure (e.g., an antigenic determinant or epitope) on the chemical species; for example, the imaging agent recognizes and binds to a specific protein structure of PSMA rather than to proteins generally.

The PSMA-specific imaging agents include three main regions: the PSMA binding region, a spacer region including the organic spacer groups and the negatively charged peptide oligomer, and the imaging group region. The PSMA binding region includes a urea ligand based on Cys-C(O)-Glu, and plays an important role in the specific binding of the imaging agent.

The spacer region serves to separate the imaging group and the PSMA binding region, but also plays a role in the specific binding of the PSMA-specific imaging agent. In addition, as described herein, the negatively charged peptide oligomer within the spacer region improves the biodistribution profile of the PSMA-specific imaging agent by reducing background binding. The negatively charged peptide oligomer is negatively charged as a result of including one or more negatively charged amino acids. Examples of negatively charged amino acids include glutamic acid and aspartic acid. A preferred negatively charged amino acid is glutamic acid, with D-glutamic acid being used in some embodiments. One or more of the amino acids making up the negatively charged peptide oligomer can be negatively charged amino acids. In a preferred embodiment, three of the amino acids are negatively charged. The amino acids are linked through peptide bonds to form a relatively short negatively charged peptide oligomer having a length of 3 to 6 amino acids. However, lengths of 3, 4, 5, 6, 3-5, 3-4, 4-5, 4-6, and 5-6 amino acids are also within the scope of the present invention. Note that further amino acids can also be present in the adjacent spacer groups.

Adjacent to the negatively charged amino acid peptide oligomer are two organic spacer groups, designated $S^1$ and $S^2$ in formula 1. The organic spacer groups $S^1$ and $S^2$ connect the negatively charged peptide oligomer to the PSMA binding region and the imaging group, respectively. The organic spacer groups can include from 5 to 30 carbons, from 5 to 15 carbons, or from 10 to 15 carbons. The organic spacer groups are primarily long alkyl chains, but in some embodiments the organic spacer group can include an aryl group such as a phenyl ring. Typically, the bulk of the organic spacer groups are formed through the reaction of amino acids with one another. Accordingly, in some embodiments, the organic spacers include one or more amino acids. The organic spacer groups can include both natural and non-natural amino acids, oligopeptides, for example, linear or cyclic oligopeptides, and nucleic acids. The organic spacer group can be a peptide or peptide moiety.

A common organic spacer for $S^1$ is an organic spacer group having the structure:

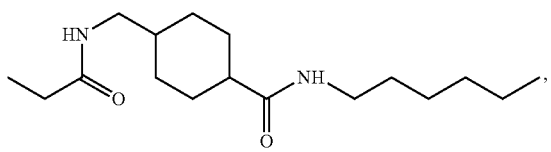 [SMILES: CCCCCCNC(=O)C1CCC(CNC(=O)CC)CC1]

while a common organic spacer for $S^2$ includes a tyrosine-lysine dipeptide.

The PSMA-specific imaging agent also includes an imaging group, which is a structure that allows the imaging agent to be detected using an appropriate imaging device. Examples of imaging agents include near infrared imaging agents, positron emission tomography imaging agents, single-photon emission tomography agents, fluorescent compounds, radioactive isotopes, and MRI contrast agents. The detectable imaging group can be any material having a detectable physical or chemical property. Such imaging groups have been well-developed and, in general, most any imaging group can be used in the present invention. Thus, an imaging group is any composition detectable by spectroscopic, photochemical, biochemical, immunochemical, electrical, optical or chemical means. The choice of imaging group depends on sensitivity required, ease of conjugation with the compound, stability requirements, available instrumentation, and disposal provisions. A comprehensive review of imaging agents and their imaging groups can be found in the Molecular Imaging and Contrast Agents Database (MICAD), developed by the National Center for Biotechnology Information, which is incorporated herein by reference.

Various fluorochromes are commercially available and can be used as near infrared imaging groups for the imaging agents of the invention. Exemplary fluorochromes include, for example, Cy5.5, Cy5 and Cy7 (GE Healthcare); AlexaFlour660, AlexaFlour680, AlexaFluor750, and AlexaFluor790 (Invitrogen); VivoTag680, VivoTag-5680, and VivoTag-5750 (PerkinElmer); Dy677, Dy682, Dy752 and Dy780 (Dyomics); DyLight547, DyLight647 (Pierce); HiLyte Fluor 647, HiLyte Fluor 680, and HiLyte Fluor 750 (AnaSpec); IRDye 800CW, IRDye 800RS, and IRDye 700DX (Li-Cor); and ADS780WS, ADS830WS, and ADS832WS (American Dye Source) and Kodak X-SIGHT 650, Kodak X-SIGHT 691, Kodak X-SIGHT 751 (Carestream Health). An example of a PSMA-specific imaging agent including a near-infrared imaging group is ZJ-MCC-dEdEdEGK(IRDye800cw)G (SEQ ID NO: 6).

In some embodiments, the imaging group comprises a radioisotope. Specific exemplary radioisotopes include $^{18}F$, $^{123}I$, $^{124}I$, $^{125}I$, $^{126}I$, $^{131}I$, $^{75}Br$, $^{76}Br$, $^{77}Br$, $^{80}Br$, $^{80m}Br$, $^{82}Br$, $^{83}$Br, $^{68}$Ga and $^{211}$At. Radioisotope containing compounds of any embodiment of the present invention can be prepared with sufficient radiolabel to be used in imaging applications. In other words, the compounds can be prepared with radioisotope concentrations greater than natural abundance, when a particular radioisotope occurs naturally.

Radiolabeled compounds may be used for diagnostic, imaging, or therapeutic purposes. For example, some compounds, e.g. those labeled with $^{125}$I and $^{123}$I, are designed for SPECT imaging, while some compounds, e.g. those labeled with $^{18}$F, $^{68}$Ga, and $^{124}$I, are designed for PET imaging, and some radioisotopically labeled compounds may be used therapeutically. In general, the suitability of a particular radioisotope for a particular purpose is well understood in the art.

In some embodiments, the imaging group is a positron or single-photon emission tomography imaging group. Examples of imaging agents including positron or single-photon emission tomography imaging group include E'E-Amc-Ahx-dEdEdEGYGGGC-NH$_2$ (SEQ ID NO: 7), E'E-Amc-Ahx-dEdEdEYK(Bn-NOTA)-NH$_2$ (SEQ ID NO: 8), and E'E-Ahx-EEEYK(Bn-NOTA)-NH$_2$ (SEQ ID NO: 9).

In some embodiments, the imaging group is suitable for use as a magnetic resonance imaging agent. Disease detection using MRI is often difficult because areas of disease have similar signal intensity compared to surrounding healthy tissue. In the case of magnetic resonance imaging, the imaging agent can also be referred to as a contrast agent. Lanthanide elements are known to be useful as contrast agents. The lanthanide chemical elements comprises the fifteen metallic chemical elements with atomic numbers 57 through 71, and include lanthanum, cerium, praseodymium, neodymium, promethium, samarium, europium, gadolinium, terbium, dysprosium, holmium, erbium, thulium, ytterbium, and lutetium. Preferred lanthanides include europium, gadolinium, and terbium. In order to more readily handle these rare earth metals, the lanthanides are preferably chelated. In some embodiments, the lanthanide selected for use as an imaging group is gadolinium, or more specifically gadolinium (III).

Methods of Imaging a Tissue Region Using a PSMA-Specific Imaging Agent

Another aspect of the invention provides a method for imaging prostate cancer in a tissue region of a subject that includes the steps of: (a) administering to the subject a detectably effective amount of a PSMA-specific imaging agent comprising a compound according to formula I:

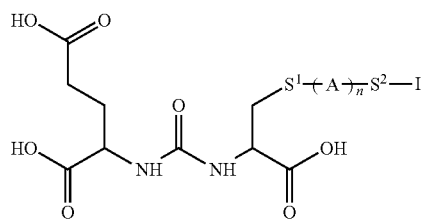

I wherein S$^1$ is an organic spacer group having from 5 to 30 carbons, A is an amino acid forming a portion of a negatively charged peptide oligomer, n is from 3 to 6, S$^2$ is an organic spacer group having from 5 to 15 carbons, and I is an imaging group, and pharmaceutically acceptable salts thereof; (b) allowing a sufficient amount of time for the PSMA-specific imaging agent to enter the tissue region; and (c) performing imaging of the tissue region of the subject using an imaging device capable of detecting the imaging group. The imaging agent can be any of the imaging agents encompassed by formula I and/or described herein. In some embodiments, the imaging device is a positron or single-photon emission tomography/computed tomography scanner, and the imaging group is a corresponding positron or single-photon emission tomography imaging group. In other embodiments, the imaging device is near-infrared imaging device, and the imaging group of the imaging agent is a near-infrared imaging group.

The present invention provides a method of generating an image of a tissue region of a subject, by administering to the subject a detectably effective amount of a PSMA-specific imaging agent, and generating an image of the tissue region of the subject to which the imaging agent has distributed. In order to generate an image of the tissue region, it is necessary for a detectably effective amount of imaging agent to reach the tissue region of interest, but it is not necessary that the imaging agent be localized in this region alone. However, in some embodiments, the PSMA-specific imaging agents are targeted or administered locally such that they are present primarily in the tissue region of interest. Examples of images include two-dimensional cross-sectional views and three dimensional images. In some embodiments, a computer is used to analyze the data generated by the imaging agents in order to generate a visual image. The tissue region can be an organ of a subject such as the heart, lungs, or blood vessels. In other embodiments, the tissue region can be diseased tissue, or tissue that is suspected of being diseased, such as a tumor or atherosclerotic tissue. Examples of imaging methods include optical imaging, computed tomography, positron emission tomography, single photon emission computed tomography, and magnetic resonance imaging.

Means of detecting labels in order to generate an image are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Finally simple colorimetric labels may be detected simply by observing the color associated with the label.

In some embodiments, the PSMA-specific imaging agent is detected using optical imaging. Optical imaging can be fast, safe, cost effective, and highly sensitive. Scan times are on the order of seconds to minutes, there is no need for ionizing radiation, and the imaging systems can be simple to use. In addition, optical probes can be designed as dynamic molecular imaging agents that may alter their reporting profiles in vivo to provide molecular and functional information in real time. In order to achieve maximum penetration and sensitivity in vivo, the choice for most optical imaging in biological systems is within the red and near-infrared (NIR) spectral region (600-900 nm), although other wavelengths in the visible region can be used. In the NIR wavelength range, absorption by physiologically abundant absorbers such as hemoglobin or water, as well as tissue autofluorescence, is minimized.

Optical imaging includes all methods from direct visualization without use of any device and use of devices such as various scopes, catheters and optical imaging equipment, for example computer based hardware for tomographic presentations. The imaging agents are useful with optical imaging modalities and measurement techniques including, but not limited to: endoscopy; fluorescence endoscopy; luminescence imaging; time resolved transmittance imaging; transmittance imaging; nonlinear microscopy; confocal imaging; acousto-optical imaging; photoacoustic imaging; reflectance spectroscopy; spectroscopy; coherence interferometry; interferometry; optical coherence tomography; diffuse optical tomography and fluorescence mediated molecular tomography (continuous wave, time domain frequency domain systems and early photon), and measurement of light scattering, absorption, polarization, luminescence, fluorescence lifetime, quantum yield, and quenching.

In other embodiments, the PSMA-specific imaging agent can be detected using computed tomography. Computed tomography (CT) refers to a diagnostic imaging tool that computes multiple x-ray cross sections to produce a cross-sectional view of the vascular system, organs, bones, and tissues. Positive emissions tomography and single photon emission computed tomography refer to a diagnostic imaging tool in which the patient receives a radioactive isotope by injection or ingestion which then computes multiple x-ray cross sections to produce a cross-sectional view of the vascular system, organs, bones, and tissues to image the radioactive tracer. These radioactive isotopes are bound to compounds or drugs that are injected into the body and enable study of the physiology of normal and abnormal tissues.

Before or during these steps, an imaging device can be positioned around or in the vicinity of a subject (for example, an animal or a human) to detect signals emitted from the subject. The emitted signals can be processed to construct an image, for example, a tomographic image. In addition, the processed signals can be displayed as images either alone or as fused (combined) images.

Another aspect of the invention provides a method of in vivo optical imaging, wherein the illuminating and detecting steps are performed using an endoscope, catheter, tomographic system, hand-held optical imaging system, or an intraoperative microscope. In certain embodiments, the method is a method of in vivo imaging, wherein the presence, absence, or level of emitted signal is indicative of a disease state. In certain embodiments, the method is a method of in vivo imaging, wherein the method is used to detect and/or monitor a disease. In certain embodiments, the disease is cancer. Another aspect of the invention provides a method of in vivo imaging, wherein the signal emitted by the agent is used to construct an image. In other embodiments, the image is a tomographic image.

An imaging system useful in the practice of the invention typically includes three basic components: (1) an appropriate source for inducing excitation of the imaging agent, (2) a system for separating or distinguishing emissions from the imaging agent, and (3) a detection system. The detection system can be hand-held or incorporated into other useful imaging devices, such as intraoperative microscopes. Exemplary detection systems include an endoscope, catheter, tomographic system, hand-held imaging system, or an intraoperative microscope.

A particularly useful emission gathering/image forming component is an endoscope. Endoscopic devices and techniques which have been used for in vivo optical imaging of numerous tissues and organs. Other types of emission gathering components are catheter-based devices, including fiber optics devices. Such devices are particularly suitable for intravascular imaging.

Once the PSMA-specific imaging agent has been administered, a sufficient amount of time for the PSMA-specific imaging agent to enter the tissue region. The time required for contrast agents to reach a tissue region are known by those skilled in the art, and can be calculated based on available software, and vary depending on the injection site and the particular tissue region.

The methods and compositions of the invention can be used to help a physician or surgeon to identify and characterize areas of disease, such as dysplasia and cancer, to distinguish diseased from normal tissues, such as detecting specific regions of prostate cancer within an organ or other tissues that are difficult to detect using ordinary imaging techniques, and to further assess said tissues as candidates for particular treatment regimens, or gauge the prognosis such as staging the cancer. The methods and compositions of the invention can also be used in the detection, characterization and/or determination of the localization of a disease, including early disease, the severity of a disease or a disease-associated condition, the staging of a disease, and/or monitoring a disease. The presence, absence, or level of an emitted signal can be indicative of a disease state.

The PSMA-specific imaging agents of the present invention can be used to image a wide variety of different types of tissue regions. Examples of different types of tissue regions include portions of the cardiovascular system, such as the heart, blood vessels, carotid arteries, and the aorta; lung tissue, adipose tissue, brain tissue, hepatic tissue, renal tissue, and prostate tissue. All of these tissues can readily be imaged by injection of the PSMA-specific imaging agents. Note that while PSMA-specific imaging agents are typically used to image a particular tissue region of interest, they can also be used to image an organ, or a whole body.

A prostate cancer tumor can be imaged using PSMA either at the prostate, or at other tissues subsequent to metastasis. Unlike many other cancers, prostate cancer is particularly difficult to detect using existing molecular imaging tracers. There are several reasons for this, including the relatively slow growth and metabolic rate of prostate cancer compared to other malignancies as well as the small size of the organ and proximity to the urinary bladder, into which most radiopharmaceuticals are eventually excreted. Accordingly, in some embodiments, the tissue region is the prostate gland.

A tumor is an abnormal mass of tissue as a result of abnormal growth or division of cells caused by cancer. Tumors can occur in a variety of different types of tissue such as the breast, lung, brain, liver kidney, colon, and prostate, can be malignant or benign, and generally vary in size from about 1 cm to about 5 cm.

The imaging methods of the invention are suitable for imaging any physiological process or disease in which PSMA is involved. Typically, imaging methods are suitable for identification of areas of tissues or targets which express high concentrations of PSMA. Typical applications include imaging malignant tumors or cancers that express PSMA, prostate cancer (including metastasized prostate cancer), and angiogenesis. Essentially all solid tumors express PSMA in the neovasculture. Therefore, methods of the present invention can be used to image nearly all solid tumors including lung, renal cell, glioblastoma, pancreas, bladder, sarcoma, melanoma, breast, colon, germ cell, pheochromocytoma, esophageal and stomach. Also, certain benign lesions and tissues including endometrium, schwannoma and Barrett's esophagus can be imaged according to the present invention. PSMA is frequently expressed in endothelial cells of capillary vessels in peritumoral and endotumoral areas of various malignancies such that compounds of the invention and methods of imaging using same are suitable for imaging such malignancies.

Cancer Treatment Using PSMA-Specific Imaging Agents

PSMA-specific imaging agents can be used in a variety of different manners to carry out or assist in cancer treatment, and in particular in prostate cancer treatment. In one aspect, the PSMA-specific imaging agents are used to identify the location and/or severity of the cancer, after which the cancer is treated using a suitable method such as surgery or chemotherapy. In another aspect, the PSMA-specific imaging agents are modified by replacing the imaging group with a toxin group so that the PSMA-specific imaging agents become PSMA-specific anticancer agents.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression. Examples of cancers are sarcoma, breast, lung, brain, bone, liver, kidney, colon, and prostate cancer.

In some embodiments, the method further includes the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, and administration of immunotoxins.

In some embodiments, the step ablating the cancer includes administering a therapeutically effective amount of an anticancer agent to the subject. Examples of anticancer agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-□, rapamycin, thapsigargin, and bikunin.

Another method of ablating cancer such as prostate cancer that has been detected using a PSMA-specific imaging agent is to conducting surgery to remove the cancer tissue (e.g., prostate cancer tissue) from the subject. The main type of surgery for prostate cancer is known as a radical prostatectomy. Radical prostatectomy involves removing the entire prostate gland plus some of the tissue around it, including the seminal vesicles. Examples of types of radical prostatectomy include radical retropubic prostatectomy, radical perineal prostatectomy, and laparoscopic radical prostatectomy.

In some embodiments, the surgery used to remove the cancer is robotic surgery that is guided by use of the PSMA-specific imaging agent. For example, the robotic surgery can be near-infrared fluorescence-guided robotic surgery. A preferred type of robotic surgery is robotic-assisted laparoscopic radical prostatectomy (RALRP). A robotic surgery system for performing robotic surgery with a surgery robot using guiding images of a part to be operated on, the robotic surgery system comprising: an endoscope apparatus for capturing medical images of a predetermined organ in a body to be examined; a non-endoscopic apparatus including at least one of an ultrasound apparatus, a computed tomography (CT) apparatus, a magnetic resonance imaging (MRI) apparatus, and a positron emission tomography (PET) apparatus for capturing medical images of the predetermined organ; a medical image processing apparatus for acquiring the medical images captured using the plurality of multi-modal medical image capturing apparatuses, extracting surface information of the predetermined organ, which is included in each of the medical images, from each of the medical images, mapping each of the medical images using the extracted surface information, and generating a synthesis image in which the medical images have been registered, based on the mapping result; a display apparatus for displaying the generated synthesis image; and the surgery robot for performing a robotic surgery. See for example US Patent Publications 2013/0035583 and 2013/0211420, the disclosures of which are incorporated herein by reference.

In some embodiments, PSMA-specific anticancer agents in which the imaging group has been replaced with a toxin are used to treat prostate cancer. In other embodiments, the PSMA-specific anticancer agents are used to treat metastatic cancer which has spread to one or more sites beyond the initial point where cancer has occurred. As noted herein, because PSMA occurs in a variety of different types of cancer, the PSMA-specific anticancer agents can be used to treat cancer other than prostate cancer.

Accordingly, in one aspect, the invention provide methods of treating tumors by administering to a subject a therapeutically effective amount of a PSMA-specific anticancer agent comprising a therapeutically effective toxin such as a radioisotope. In certain embodiments, the tumor cells may express PSMA, such as prostate tumor cells or metastasized prostate tumor cells. In other embodiments, a tumor may be treated by targeting adjacent or nearby cells which express PSMA. For example, vascular cells undergoing angiogenesis associated with a tumor may be targeted. Essentially all solid tumors express PSMA in the neovasculture. Therefore, methods of the present invention can be used to treat nearly all solid tumors including lung, renal cell, glioblastoma, pancreas, bladder, sarcoma, melanoma, breast, colon, germ cell, pheochromocytoma, esophageal and stomach. Also, certain benign lesions and tissues including endometrium, schwannoma and Barrett's esophagus can be treated according to the present invention. Examples of therapeutically effective radioisotopes include $^{131}$I and $^{211}$At.

Administration and Formulation of PSMA-Specific Imaging and Anticancer Agents

In some embodiments, the PSMA-specific imaging agent is administered in a pharmaceutically acceptable carrier, e.g., an aqueous carrier. A variety of carriers can be used, e.g., buffered saline and the like. These solutions are sterile and generally free of undesirable matter. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration and imaging modality selected.

Administration of the PSMA-specific imaging agent for in vivo imaging of a tissue, an organ or a full body can include a) providing a pharmaceutical formulation comprising the imaging agent of the invention and a pharmaceutically acceptable excipient, wherein the imaging agent is formed according to any of the above described embodiments, and wherein the formulation is suitable for administration as a PSMA-specific imaging agent and the imaging agent is present in a detectably effective amount; b) providing an imaging device (i.e., an optical imaging device); c) administering the pharmaceutical formulation in an amount sufficient to generate the tissue or body image; and d) imaging the distribution of the pharmaceutical formulation of step a) with the imaging device, thereby imaging the tissue, organ or body.

The pharmaceutical formulations of the invention can be administered in a variety of unit dosage forms, depending upon the particular tissue or cancer to be imaged, the general medical condition of each patient, the method of administration, and the like. Details on dosages are well described on the scientific and patent literature. The exact amount and concentration of PSMA-specific imaging agent or pharmaceutical of the invention and the amount of formulation in a given dose, or the "detectably effective dose" can be routinely determined by, e.g. the clinician. The "dosing regimen" will depend upon a variety of factors, e.g. whether the tissue region or tumor to be imaged is disseminated or local, the general state of the patient's health, age and the like. Using guidelines describing alternative dosing regimens, e.g. from the use of other imaging agents, the skilled artisan can determine by routine trials optimal effective concentrations of pharmaceutical compositions of the invention.

The pharmaceutical compositions of the invention can be delivered by any means known in the art systematically (e.g. intravenously), regionally or locally (e.g. intra- or perituomoral or intracystic injection, e.g. to image bladder cancer) by e.g. intraarterial, intratumoral, intravenous (iv), parenteral, intrapneural cavity, topical, oral or local administration, as sub-cutaneous intra-zacheral (e.g. by aerosol) or transmucosal (e.g. voccal, bladder, vaginal, uterine, rectal, nasal, mucosal), intra-tumoral (e.g. transdermal application or local injection). For example, intra-arterial injections can be used to have a "regional effect", e.g. to focus on a specific organ (e.g. brain, liver, spleen, lungs).

Preparation of the Compounds

PSMA-specific imaging agents may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

Those skilled in the art will appreciate that synthetic routes other than those described in the examples herein may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1: Improving the Biodistribution of PSMA-Targeting Tracers with a Highly Negatively Charged Linker Prostate specific membrane antigen (PSMA) is overexpressed in prostate cancer and in tumor vasculature. Small molecule based inhibitors of PSMA have promised to provide sensitive detection of primary and metastatic prostate tumors. Although significant progress has been made, many of the radiolabeled imaging agents exhibit non-specific background binding. Prevailing tracer designs focus on high affinity urea-based inhibitors with strategically placed hydrophobic patches that interact favorably with the substrate tunnel of PSMA. The inventors hypothesized that a novel PSMA inhibitor design incorporating highly negatively charged linkers may minimize non-specific binding and decrease overall background.

Materials and Methods:

(S)-2-(3-((S)-5-amino-1-carboxypentyl)ureido)pentanedioic acid (Cys-C(O)-Glu) was custom-made by Bachem Bioscience Inc. H-Glu(OtBu)-OtBu is from Bachem (King of Prussia, Pa.). N—[N—[(S)-1,3-dicarboxypropyl] carbamoyl]-S-[$^3$H]-methyl-L-cysteine was custom made by GE Healthcare Life Sciences. Succinimidyl 4-(N-maleimidomethyl)cyclohexane-1-carboxylate (SMCC) was purchased from Thermo Fisher Scientific, Rockford, Ill. Rink Amid MBHA resin, and Fmoc-(D)Glu(OtBu)-OH, Fmoc-Gly-OH, Fmoc-Tyr(tBu)-OH, Fmoc-Cys(Trt)-OH were purchased from Peptides International Inc, Louisville Ky. The Fmoc-Glu-OtBu was from Novabiochem, Merck KGaA, Darmstadt, Germany. All the other chemicals were purchased from Sigma-Aldrich Inc., St. Louis, Mo. High resolution matrix-assisted laser desorption/ionization mass (MALDI-MS) spectra were obtained from an Applied Biosystems 4800 MALDI/TOF Analyzer in positive ion mode.

High Performance Liquid Chromatography (HPLC) was performed on a Shimadzu HPLC system equipped with a SPD-20V prominence UV/visible detector and monitored at a wavelength of 260 nm. Preparative HPLC was achieved using a SymmetryPrep™ C18 column (100 mm×19 mm×5 µm, Waters Corporation, Milford, Mass., USA) at a flow rate of 3.0 ml/min. Analytical HPLC was performed using an analytical Symmetry C18 column (150 mm×4.6 mm×5 µm, Waters Corporation, Milford, Mass., USA). Flow rate is 1.0 mL/min unless otherwise specified.

Synthesis of Compound 1 (ZJ-MCC-Ahx-dEdEdEG (SEQ ID NO: 10)): The peptide Fmoc-Ahx-dGlu-dGlu-dGlu-G was assembled on a Wang resin. The three glutamates (dGlu) are of D-isoform. Peptide synthesis was carried out manually by Fmoc chemistry with HCTU (2-(6-Chloro-1H-benzotriazole-1-yl)-1,1,3,3-tetramethylaminium hexafluorophosphate) activation. Generally, peptides were synthesized at a 0.01 mmol scale starting from the C-terminal amino acid on solid support. Fmoc-deprotection at each cycle was carried out using 20% piperidine in DMF. Coupling reactions were carried out using 3.3 eq. of Fmoc-amino acids in DMF activated with 3.3 eq. of HCTU and 5 equivalents of diisopropylethylamine (DIPEA) in DMF. These steps were repeated each time with an amino acid added. After the peptide sequence was built on the resin, the Fmoc group of the N-terminal amino acid was deprotected. Coupling of 4-(N-maleimidomethyl)cyclohexane-1-carboxylate (SMCC) to the N-terminal amine group was achieved with 3.3 equivalents of SMCC in DMF. Coupling of Cys-C(O)-Glu was performed using 3.3 equivalents of Cys-C(O)-Glu in DMF after coupling SMCC to the peptide. The final peptide resin was washed with DMF and then dichloromethane and dried. Cleavage and deprotection were carried out using TFA/water/triisopropylsilane (950:25:25) for 1 h, the resin was removed by filtration and washed with TFA. The combined filtrate was dried under nitrogen. The synthesized peptide was precipitated by the addition of diethyl ether and collected by centrifugation. The cleaved peptide was purified by preparative HPLC. The products were ascertained by high resolution matrix-assisted laser desorption/ionization mass (MALDI-MS) spectra. Then Fmoc was deprotected followed by coupling of SMCC and Cys-C(O)-Glu. The product has retention time of 11.9 minutes on analytical HPLC with 0-55% gradient over 45 minutes (flow rate 1 ml/min; A: 10 mM triethylammonium acetate TEAA, pH 7.0; B was acetonitrile.) The mass was verified by MALDI/TOF mass spectrometry—Calculated: 1088.4 (C44H64N8O22S), Found m/z: 1089.4 (M+1).

Compound 2—(ZJ-MCC-Ahx-YYYG (SEQ ID NO: 2)): The peptide Fmoc-Ahx-Tyr-Tyr-Tyr-Gly (SEQ ID NO: 11) was assembled on Wang resin. Then Fmoc was deprotected followed by coupling of SMCC and Cys-C(O)-Glu as described for compound 1. The product has retention time of 14.9 minutes on analytical HPLC with 0-55% gradient over 45 minutes (flow rate 1 ml/min; A: 10 mM triethylammonium acetate TEAA, pH 7.0; B was acetonitrile.) The mass was verified by MALDI/TOF mass spectrometry—Calculated: 1190.5 (C56H70N8O19S), Found m/z: 1191.4 (M+1).

Synthesis of Compound 3: E'E-Amc-Ahx-dEdEd-EGYGGGC-NH$_2$ (SEQ ID NO: 7)

Fmoc-'E-Amc-Ahx-dGlu-dGlu-dGlu-Gly-Tyr-Gly-Gly-Gly-Cys-NH$_2$ (SEQ ID NO: 12) was assembled on the resin using standard Fmoc peptide synthesis. Fmoc-'E stands for Fmoc(Glu)-OtBu where the gamma-carboxyl group is unprotected. After removal of the last Fmoc on the assembled peptide, the resin is washed with DMF, methanol and chloroform. Then, a chloroform solution containing a 5-fold excess of H-Glu(OtBu)-OtBu mixed with 2.5 eq (with respect to H-Glu(OtBu)-OtBu) of diisopropylethylamine was prepared. The solution was then added slowly to 0.25 eq (with respect to H-Glu(OtBu)-OtBu) triphosgene over 10 minutes at room temperature. The presumed product of this reaction is an isocyanate derivative of H-Glu(OtBu)-OtBu. After a 15 minute incubation to allow for isocyanate formation, the reaction is mixed with the 'E-Amc-Ahx-Glu-Glu-Glu-Gly-Tyr-Gly-Gly-Gly-Cys-NH$_2$ (SEQ ID NO: 13) on a rink amide resin pre-swollen in chloroform with 2.5 eq of diisopropylethylamine. After 30 minutes of mixing, a Ninhydrin test was administered to test for residual free-amine on the resin. Once the reaction is complete, the resin is washed and the complete peptide product is cleaved. The product elutes at 12.4 minutes on analytical HPLC column with a 10%-95% gradient in 40 minutes (flow rate 0.8 ml/min; A: water with 0.1% TFA; B: acetonitrile). The mass was verified by MALDI/TOF mass spectrometry—Calculated: 1452.6 (C60H88N14O26S), found m/z: 1453.4 (M+1).

[$^{99m}$Tc]3: Tc99m Labeling of Compound 3

The procedure was modified from that used by Tolmacheva and coworkers for Affibody labeling. Ahlgren et al., Nuclear medicine and biology; 37(5):539-546 (2010). An aqueous solution of peptide compound 6 (20 µL 0.5 mM) was first mixed with 10 µL of EDTA (10 mg/mL), 10 µL of sodium gluconate (375 mg/mL) and 10 µL stannous chloride (7.5 mg/mL in 10 mM HCl). Then 10-12 mCi of freshly eluted $^{99m}$Tc pertechnetate was added and the solution was heated to 95° C. for 1 hour. The labeling mixture was loaded on a SepPak cartridge, and washed with 3 mL of saline twice. The radiolabeled [$^{99m}$Tc]3 is then eluted with 1 mL of 100% ethanol. The ethanol is evaporated and the remaining solid is dissolved in saline and analyzed by TLC. Radiochemical purity by TLC is typically 95%.

Synthesis of Compound 4: E'E-Amc-Ahx-dEdEdEYK(Bn-NOTA)-NH$_2$ (SEQ ID NO: 8)

Fmoc-'E-Amc-Ahx-dGlu-dGlu-dGlu-Tyr-Lys-NH$_2$ (SEQ ID NO: 14) was assembled on the resin using standard Fmoc peptide synthesis. The glutamates (dGlu) are D-isomers. Fmoc-'E stands for Fmoc(Glu)-OtBu where the gamma-carboxyl group is unprotected. The last Fmoc on the assembled peptide is then removed by 20% piperidine. Then a chloroform solution containing 5 eq. of H-Glu(OtBu)-OtBu mixed with 2.5 eq (with respect to H-Glu(OtBu)-OtBu) of diisopropylethylamine was prepared. The solution was then added slowly to 0.25 eq (with respect to H-Glu (OtBu)-OtBu) triphosgene in chloroform over 10 minutes at room temperature. After a 15 minute incubation to allow for isocyanate formation, the reaction is mixed with the 'E-Amc-Ahx-Glu-Glu-Glu-Gly-Tyr-Gly-Gly-Gly-Cys-NH$_2$ (SEQ ID NO: 13) on a rink amide resin pre-swollen in chloroform with 2.5 eq of diisopropylethylamine. After 30 minutes of mixing, a Ninhydrin test was administered to test for residual free-amine on the resin. The reaction was repeated if needed. Once the reaction is complete, the resin is washed and the complete peptide product is cleaved. To couple the purified peptide E'EAmc-Ahx-EEEYK(Bn- NOTA)-NH$_2$ (SEQ ID NO: 15) with SCN-Bn-NOTA (Macrocyclics), E'EAmc-Ahx-dEdEdEYK (SEQ ID NO: 16) was dissolved in DMF at a concentration of 25 mg/mL and an equimolar amount of SCN-Bn-NOTA was dissolved in DMSO at a concentration of 200 mg/mL. After mixing the above DMF and DMSO solutions of the reactants, DIPEA was added to concentration of 2% v/v. The reaction was monitored by HPLC and allowed to proceed up to 2 hours. Then, glacial acetic acid equivolume to DIPEA is added to stop the reaction. The final product was E'EAmc-Ahx-dGlu-dGlu-dGlu-Tyr-Lys(Bn-NOTA)-NH$_2$ (compound 4) (SEQ ID NO: 8) The product elutes at 14.8 min on an analytical column with a 10%-90% gradient in 45 minutes with a flow rate of 0.8 ml/min (A: water with 0.1% TFA; B: acetonitrile). The mass was verified by MALDI/TOF mass spectrometry—Calculated: 1699.7, found m/z: 1700.7 (M+1).

Synthesis of Compound 5: E'E-Ahx-EEEYK(Bn-NOTA)-NH$_2$ (SEQ ID NO: 9)

Fmoc-'E-Ahx-Glu-Glu-Glu-Tyr-Lys-NH$_2$ (SEQ ID NO: 17) was assembled on the resin using standard Fmoc peptide synthesis. The Glutamates are L-isomers. Fmoc-'E stands for Fmoc(Glu)-OtBu where the gamma-carboxyl group is unprotected. The last Fmoc on the assembled peptide is then removed by 20% piperidine. Then, a chloroform solution containing 5 eq of H-Glu(OtBu)-OtBu mixed with 2.5 eq (with respect to H-Glu(OtBu)-OtBu) of diisopropylethylamine was prepared. The solution is then added slowly to 0.25 eq. (with respect to H-Glu(OtBu)-OtBu) triphosgene in chloroform over 10 minutes at room temperature. After a 15 minute incubation to allow for isocyanate formation, the reaction is mixed with the 'E-Amc-Ahx-Glu-Glu-Glu-Gly-Tyr-Gly-Gly-Gly-Cys-NH$_2$ (SEQ ID NO: 13) on a rink amide resin pre-swollen in chloroform with 2.5 eq. of diisopropylethylamine. After 30 minutes of mixing, a Ninhydrin test was administered to test for residual free-amine on the resin. Once the reaction was complete, the resin was washed and the complete peptide product was cleaved. The product was then purified by HPLC with acetonitrile/water with 0.1% TFA. Coupling of the purified peptide E'E-Ahx-EEEYK(Bn-NOTA)-NH$_2$ (SEQ ID NO: 9) with SCN-Bn-NOTA (Macrocyclics) was performed with a method derived from Lang et. al. Lang et al., Bioconjug Chem; 22(12): 2415-2422 (2011). Briefly, E'E-Ahx-EEEYK (SEQ ID NO: 18) was dissolved in DMF at concentration of 25 mg/mL and an equimolar amount of SCN-Bn-NOTA was dissolved in DMSO at a concentration of 200 mg/mL. After mixing the above DMF and DMSO solutions of the reactants, DIPEA was added to concentration of 2% v/v. The reaction was monitored by HPLC and allowed to proceed up to 2 hours. Then, glacial acetic acid equivolume to DIPEA was added to stop the reaction. The final product E'E-Ahx-Glu-Glu-Glu-Tyr-Lys(Bn-NOTA)-NH$_2$ (compound 5) (SEQ ID NO: 9) elutes at 13.4 minutes on a (10% B-95% B HPLC gradient in 40 minutes with a flow rate of 0.8 ml/min on an analytical column. (A: water with 0.1% TFA, B: acetonitrile) The mass was verified by MALDI/TOF mass spectrometry—Calculated: 1560.6, found m/z: 1561.7 (M+1).

$^{18}$F Labeling of Compound 5

1Ci of $^{18}$F sodium fluoride in water was purchased from Siemens PETNET Solutions in Cleveland, Ohio. The activity was loaded onto a QMA column and eluted with a 200 µL fraction of saline. 15 µL of the fraction containing the highest radioactivity was added to a solution containing 6 µL of 2 mM AlCl$_3$ in 100 mM NaOAc, 2 µL of ascorbic acid (50 mg/mL in water), 20 nmol of E'E-Ahx-EEEYK(Bn-NOTA)-NH$_2$ (compound 5) (SEQ ID NO: 9) dissolved in 20 µL of water and 4 µL of 1M sodium acetate pH 4.1. The total volume of the solution was 40 µL. The solution was heated on a 105° C. heating block for 15 minutes. The reaction mixture was purified with analytical HPLC using 15% B for 5 minutes followed by 20% B (flow rate 1 min/min, A: water 0.1% TFA; B: acetonitrile). Un-reacted compound 8 elutes at 13.6 minutes. Radiolabeled [Al$^{18}$F]5 elutes at 10.7 minutes. The purified fraction is diluted ⅓ with mobile phase (0.1% TFA water) and loaded onto SepPak. The SepPak column was washed with 3 mL water and eluted with 1 mL of 90% ethanol and 10% mobile phase. The typical decay-corrected radiochemical yield is 10%. The ethanol and TFA in the collected fraction were evaporated and normal saline was added to titrate the dose.

Cell Culture

The prostate cancer cell line LNCaP (PSMA-positive) was obtained from American Type Culture Collection (Manassas, Va.). Retrovirally transformed PSMA positive PC3-PIP cells and transfection controlled PC3-flu cells were obtained from Dr. Michel Sadelain (Laboratory of Gene Transfer and Gene Expression, Gene Transfer and Somatic Cell Engineering Facility, Memorial-Sloan Kettering Cancer Center, New York, N.Y.). Cells were grown at 37° C. and 5% CO$_2$ under a humidified atmosphere. Cells were maintained in RPMI1640 medium supplemented with 2 mM L-glutamine and 10% Fetal Bovine Serum.

Competitive Binding Assay

Briefly, LNCaP or PC3-PIP cells (5×10$^5$) were incubated with different concentrations of ligands in the presence of 12 nM N—[N—[(S)-1,3-dicarboxypropyl]carbamoyl]-S-[$^3$H]-methyl-L-cysteine in a total volume of 300 µL for 1 hour at 37° C. The mixture was centrifuged at 3,000 g for 5 min at 4° C., then washed three times with 500 µL of cold PBS. Finally, 4 mL of EcoLume™ cocktail (MP Biomedicals) was added, and radioactivity was counted by scintillation counter. The concentration required to inhibit 50% of binding was determined (IC$_{50}$) by Graph Pad Prism 3.0.

SPECT/CT and Biodistribution Study of [$^{99m}$Tc]3

Male NOD scid gamma (NSG) mice bearing PC3-PIP (PSMA+) and PC3-flu (PSMA−) tumor xenografts were used for imaging. The mice were injected with 3 mCi of [$^{99m}$Tc]3. Four hours after tracer injection, SPECT/CT images were acquired using a high-resolution multi-pinhole SPECT with collimation insert with a clinical SPECT/CT scanner (Symbia T6, Siemens Molecular Imaging). DiFilippo, F. P. Phys Med Biol 53(15): 4185-4201 (2008). For the biodistribution study without imaging, male NSG mice bearing two PC3-PIP tumors were injected with 50-100 □Ci of [$^{99m}$Tc]3. Mice were sacrificed at 2 hours, 4 hours and 6 hours after injection. After thoracotomy, blood was first withdrawn from the heart, then the organs were resected en-block. The activities were counted with a Perkin Elmer 2480 Automatic Gamma Counter. The decay corrected percent injected dose per gram of organ weight (wet) (% ID/g) was calculated.

Positron emission tomography and biodistribution study of [Al$^{18}$F]5: Male NSG mice at least 6 weeks old were subcutaneously implanted with two human PC3-PIP (PSMA+) tumor xenografts. When one of the tumors reached 0.5 mL in volume, imaging and biodistribution studies were conducted. For imaging, 0.3-0.4 mCi of [Al$^{18}$F]5 was injected via the tail vein. The mouse was anesthetized with isoflurane and imaged at 1 hour post injection on a clinical PET/CT scanner (Biograph mCT, Siemens Molecular Imaging, Hoffman Estates, Ill.) using super-resolution sampling and iterative deconvolution processing. For the biodistribution study without imaging, 50-150 µCi of [Al$^{18}$F]5 was injected in PC3-PIP tumor bearing mice which were sacrificed at one and two hours post injection for biodistribution measurements.

Results:

Binding affinities of new compounds to PSMA. The equilibrium competitive binding studies of all the compounds synthesized are summarized in Table 1. All of the tested compounds exhibited similar affinity as shown in Table 1.

Figure 2:
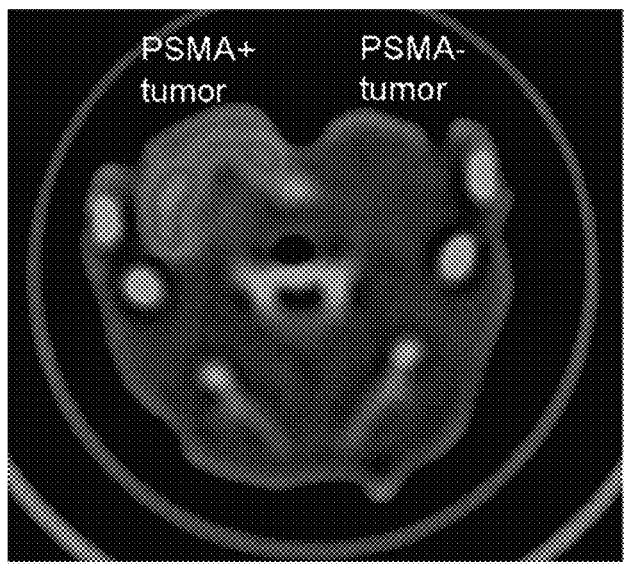
FIG. 2 shows a MicroSPECT/CT image of an NSG mouse with PC3-PIP(PSMA+) and PC3-flu(PSMA−) xenographs. Images were acquired 4 hours after tail vein injection of radiolabled [$^{99m}$Tc]3. (Left) an axial slice of SPECT/CT through the axillary region of the mouse demonstrating a PSMA+ tumor on the right side and a PSMA− tumor on the left side. (Right) a maximum intensity projection (MIP) image of the mouse. Expected normal physiologic accumulation is noted in the kidneys, bowel and bladder in addition to the PSMA+ tumor. The images demonstrate near background tracer uptake in the PSMA negative tumors, liver, lung, heart and spleen.
Figure 2:
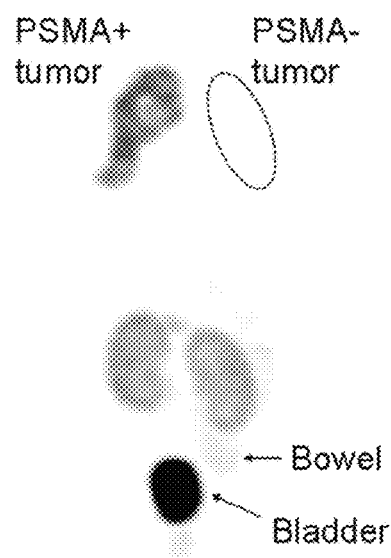

Labeling with technetium typically yields 95% radiochemical purity after SepPak purification. The imaging studies (FIG. 2) demonstrated specific targeting of PSMA+ PC3-PIP tumors with no significant binding to PC3-flu tumors. The kidneys and bladder are the most prominent organs on the images, because PSMA is expressed naturally in mouse kidneys and because it is a renally excreted compound. The amount of tracer in the measured tissue and

TABLE 1

IC$_{50}$ of compounds. 95% confidence intervals are reported in parentheses.

|  | SEQ ID NO: | IC$_{50}$ [nM] |
|---|---|---|
| ZJ-MCC-Ahx-dEdEdEG (Compound 1) | 10 | 2.2 (0.83-5.5) |
| ZJ-MCC-Ahx-YYYG (Compound 2) | 2 | 2.5 (1.1-5.6) |
| E'EAmc-Ahx-dEdEdEGYGGGC-NH$_2$ (Compound 3) | 7 | 7.0 (0.72-14) |
| E'EAmc-Ahx-dEdEdEYK(Bn-NOTA)-NH$_2$ (Compound 4) | 8 | 4.6 (1.6-6.1) |
| E'E-Ahx-EEEYK(Bn-NOTA)-NH$_2$ (Compound 5) | 9 | 4.3 (0.78-14) |
| ZJ24 (the "parent" di-amino acid urea ligand (S)-2-(3-((S)-5-amino-1-carboxypentyl)ureido)pentanedioic acid) |  | 4.3 (2.1-9.1) |

Synthesis of Tc99m Tracer:

Using RBI-1033 as a template, the inventors started their iterative re-design by considering peptide mimics of the 2-5 Å moiety (FIG. 1). One possible type of interaction between the 2-5 Å moiety and the tunnel may be a charge-charge interaction through the negatively charged phosphate backbone and the interaction of aromatic amino acid residues of PSMA with the adenine moiety. The inventors hypothesized that ZJ-MCC-Ahx-dEdEdEG (compound 1) (SEQ ID NO: 10), which has three glutamic acids, can mimic the negative charge of the phosphate backbone of 2-5 Å. ZJ-MCC-Ahx-YYYG (compound 2) (SEQ ID NO: 2) was also synthesized, which has tyrosine residues, to mimic the potential hydrogen bonding and pi-pi interaction of the nucleoside component of the 2-5 Å moiety of RBI-1033. Both demonstrated affinity comparable to the parent urea ligand MeS-Cys-C(O)-Glu (ZJ24) (Table 1).

The inventors decided to continue the iterative design process using ZJ-MCC-Ahx-dEdEdEG (compound 1) (SEQ ID NO: 10) as a template. To streamline the synthesis and to decrease cost, the SMCC based linker was modified between the tri-glutamate and the urea moiety. The thioether bond was replaced and the succinimide with a glutamyl side chain that is covalently linked to N-aminomethyl cyclohexanoic acid (Amc) via a peptide bond (FIG. 1). Compared to SMCC, this arrangement reduces steric hindrance by eliminating one side of the succinimide and shortens the linker by one carbon-carbon bond. The changes also allow the entire compound to be synthesized on the solid phase. To make a $^{99m}$Tc binding tracer from the peptide framework, a Gly-Tyr spacer was added between the triglutamate moiety and an N3S1 technetium chelate consisting of a Gly-Gly-Gly-Cys peptide (FIG. 1) (SEQ ID NO: 19). The modifications resulted in E'EAmc-Ahx-dEdEdEGYGGGC (compound 3) (SEQ ID NO: 3). The inventors used the 280 nm absorption of the tyrosine residue for concentration measurements to standardize the preparation. The affinity of the unlabeled compound is equivalent to compound 1 (Table 1). SPECT/CT imaging and biodistribution study of $^{99m}$Tc-E'EAmc-Ahx-dEdEdEGYGGGC ([$^{99m}$Tc]3) (SEQ ID NO: 20)

organs did not change significantly from 2 hours to 6 hours. Tumor uptake is 6.0±1.6% at 2 hours, 6.0±2.2% at 4 hours and 5.7%±2.5% at 6 hours (Table 2). There is a small amount of radioactivity in the thyroid (0.3% ID/g) and the stomach (0.2% ID/g) which is indicative of the presence of $^{99m}$Tc-pertechnetate. This is likely related to residual pertechnetate after cartridge purification and dissociation of technetium from the chelate. Attempts were made to use HPLC purification with C18 columns, however, the $^{99m}$Tc-labeled complex is not stable under solvent conditions for HPLC, which contains 0.1% trifluoroacetic acid.

TABLE 2

Biodistribution of [$^{99m}$Tc]3
(Unit: % ID/g; N = 6 for tumor, N = 3 for other organs)

|  | 2-hour | 4-hour | 6-hour |
|---|---|---|---|
| Tumor (PC3-PIP) | 6.03% ± 1.63% | 5.95% ± 2.23% | 5.71% ± 2.53% |
| Thyroid | 1.47% ± 0.77% | 0.28% ± 0.14% | 0.33% ± 0.30% |
| Heart | 0.21% ± 0.02% | 0.04% ± 0.01% | 0.03% ± 0.01% |
| Liver | 0.28% ± 0.07% | 0.09% ± 0.03% | 0.08% ± 0.04% |
| Bone (femur) | 0.12% ± 0.04% | 0.07% ± 0.07% | 0.06% ± 0.08% |
| Stomach | 1.00% ± 0.33% | 0.19% ± 0.12% | 0.20% ± 0.17% |
| Blood | 0.27% ± 0.08% | 0.04% ± 0.00% | 0.05% ± 0.03% |
| Small Intestine | 0.24% ± 0.11% | 0.06% ± 0.00% | 0.06% ± 0.00% |
| Large Intestine | 0.60% ± 0.36% | 0.82% ± 0.23% | 0.57% ± 0.34% |
| Kidney | 60.58% ± 18.10% | 16.06% ± 20.05% | 17.43% ± 18.92% |
| Spleen | 1.14% ± 0.30% | 0.18% ± 0.11% | 0.20% ± 0.09% |
| Pancreas | 0.18% ± 0.04% | 0.04% ± 0.02% | 0.03% ± 0.03% |
| Lung | 0.35% ± 0.06% | 0.09% ± 0.05% | 0.09% ± 0.05% |
| Muscle | 0.11% ± 0.01% | 0.04% ± 0.03% | 0.03% ± 0.04% |
| Tumor:bone | 50:1 | 85:1 | 95:1 |
| Tumor:blood | 22:1 | 149:1 | 114:1 |
| Tumor:muscle | 55:1 | 149:1 | 190:1 |
| Tumor:liver | 22:1 | 66:1 | 71:1 |

Synthesis of $^{18}$F labeled PSMA targeting tracer.

To accurately estimate the biodistribution of the highly negatively charged tracer, high radiochemical purity was needed. Since preparation of [$^{99m}$Tc]3 without $^{99m}$Tc-pertechnetate was not possible, the inventors searched for another radiolabeling strategy. Aluminum-fluoride-NOTA complex based $^{18}$F labeled peptides, first demonstrated by McBride et. al., are stable enough for purification with HPLC with 0.1% TFA in the solvent. McBride et al., J Nucl Med; 50(6):991-998 (2009). The labeled complex also results in an easily prepared $^{18}$F labeled tracer that can be used for positron emission tomography. To incorporate a NOTA chelate, the sequence Gly-Tyr-Gly-Gly-Gly-Cys (SEQ ID NO: 21) associated with the N3S1 chelate for $^{99m}$Tc was replaced with a simple Tyr-Lys. The lysine is used for coupling with a commercially available activated NOTA chelate. The resulting Compound 4: E'EAmc-Ahx-dEdEdEYK(Bn-NOTA) (SEQ ID NO: 22) can be labeled after 15 minutes of heating with 18F fluoride and aluminum chloride in acetate buffer. The resulting radioactive complex $^{18}$F aluminum-fluoride-E'EAmc-Ahx-dEdEdEYK(Bn-NOTA) (SEQ ID NO: 23) can be easily purified with HPLC. To further reduce hydrophobicity, the Amc moiety was eliminated from the linker of compound 4. The purpose of the Amc was to mimic the cyclohexane portion of the linker in RBI-1033. The inventors also changed the glutamate from D-glutamate to L-glutamate to reduce the cost of synthesis. They previously demonstrated that one can switch the conformation of the three glutamates from the D-isomer to the L-isomer without change in affinity and imaging characteristics of NIR PSMA targeting tracers. The resulting compound 5 (E'E-Ahx-EEEYK(Bn-NOTA) (SEQ ID NO: 5)), which is cheaper and more convenient to produce, has the same affinity for PSMA as compound 4 (E'E-Amc-AhxdEdEdEYK(Bn-NOTA) (SEQ ID NO: 22)). The inventors proceeded to perform PET imaging and a biodistribution study with the $^{18}$F labeled aluminum-fluoride-compound 5 ([Al$^{18}$F]5).

Figure 3:
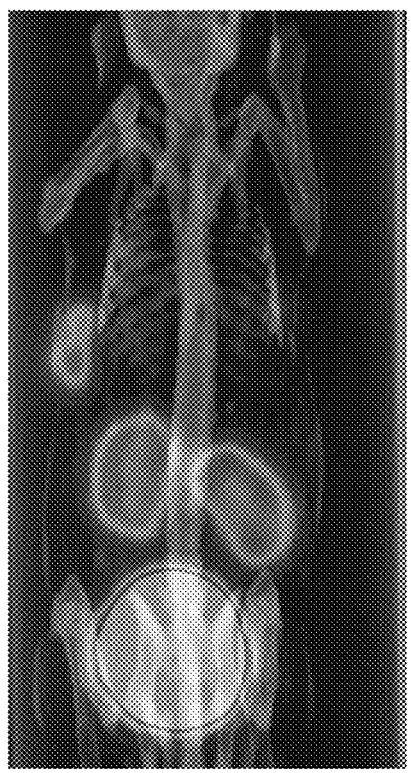
FIG. 3 provides a PET/CT image of an NSG mouse with two PC3-PIP(PSMA+) xenographs. Images were acquired 1 hours after tail vein injection of [Al$^{18}$F]5. The middle panel is maximum intensity projection image (MIP); the left panel is MIP overlayed with CT. The actual tumors are shown in the right panel. The smaller tumor has a maximum dimension of 3 mm. Expected normal physiologic accumulation is noted in the kidneys and bladder. The images demonstrate minimal background tracer uptake in the liver, lung, heart and spleen.
Figure 3:
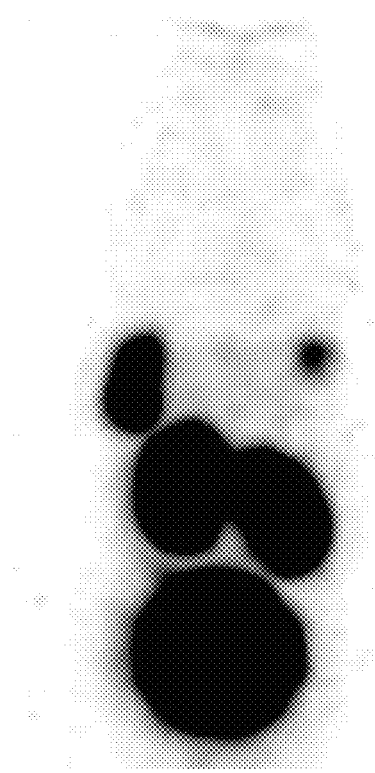
Figure 3:
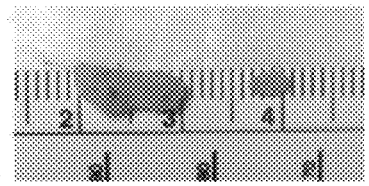

The one-hour post injection images (FIG. 3) demonstrate uptake in the PC3-PIP tumor and renal parenchyma and accumulation in the renal collecting systems and bladder. No significant tracer activity is seen in other tissue. The biodistribution data for [Al$^{18}$F]5 indicated very fast renal excretion with the amount of radioactivity in blood, bone and muscle dropping to 0.04% ID/g, 0.1% ID/g and 0.01% ID/g respectively at 2 hours post injection (Table 3). The tumor uptake was 4.6% ID/g at 2 hours. The thyroid and stomach uptake that was seen with [$^{99m}$Tc]3 were reduced to background as expected. The minimal bone uptake indicated no significant dissociation of $^{18}$F-fluoride from the complex.

TABLE 3

Preliminary 1-hour and 2-hour biodistribution of F-18 labeled [Al$^{18}$F]5 (Unit: % ID/g)

|  | 1 hour (n = 4 for tumor, n = 2 for organ) | 2 hour (n = 6 for tumor; n = 3 for organ) |
|---|---|---|
| Tumor (PC3PIP) | 6.91% ± 1.44% | 4.58% ± 0.55% |
| Thyroid | 0.11% ± 0.02% | 0.05% ± 0.00% |
| Heart | 0.14% ± 0.11% | 0.04% ± 0.01% |
| Liver | 0.41% ± 0.10% | 0.17% ± 0.03% |
| Bone | 0.39% ± 0.28% | 0.10% ± 0.02% |
| Stomach | 0.10% ± 0.03% | 0.03% ± 0.02% |
| Blood | 0.18% ± 0.09% | 0.04% ± 0.01% |
| Small Intestine | 0.43% ± 0.51% | 0.18% ± 0.02% |
| Kidney | 16.82% ± 5.60% | 5.96% ± 2.17% |
| Spleen | 0.29% ± 0.14% | 0.10% ± 0.04% |
| Lung | 0.21% ± 0.05% | 0.07% ± 0.04% |
| Muscle | 0.19% ± 0.12% | 0.01% ± 0.00% |
| Tumor:bone | 18:1 | 46:1 |
| Tumor:blood | 38:1 | 115:1 |

TABLE 3-continued

Preliminary 1-hour and 2-hour biodistribution of F-18 labeled [Al$^{18}$F]5 (Unit: % ID/g)

|  | 1 hour (n = 4 for tumor, n = 2 for organ) | 2 hour (n = 6 for tumor; n = 3 for organ) |
|---|---|---|
| Tumor:muscle | 36:1 | 458:1 |
| Tumor:liver | 17:1 | 27:1 |
| Tumor:spleen | 24:1 | 46:1 |

Discussion
Affinity vs. Background

There is growing recognition of the problem of nonspecific background binding in the initial human trials of PET and SPECT tracers targeting PSMA. Reske et al., Eur J Nucl Med Mol Imaging; 40(6):969-970 (2013). Afshar-Oromieh et al., Eur J Nucl Med Mol Imaging; 40(6):971-972 (2013).

Among the published images, there appear to be two general patterns of nonspecific uptake. One is in the salivary glands, lacrimal glands and liver such as those demonstrated by $^{123}$I-MIP-1072, $^{123}$I-MIP-1095, Glu-NH—CO—NH-Lys (Ahx)-[$^{68}$Ga(HBED-CC)]. Barrett et al., J Nucl Med; 54(3): 380-387 (2013). The other is elevated blood pool background activity, such that exhibited by $^{18}$F-DCFBC and $^{68}$Ga-DOTA-DUPA-Pep. Cho et al., J Nucl Med; 53(12): 1883-1891 (2013). There is no clear correlation between molecular structure and patterns of nonspecific activity. However, hydrophobic patches within the molecules could be the reason for nonspecific binding. The existing literature emphasizes the construction of high affinity PSMA ligands by judicious placement of hydrophobic moieties. Barinka et al. uncovered an accessory hydrophobic pocket near the S1 site of the PSMA enzymatic pocket. Barinka et al., J Med Chem; 51(24):7737-7743 (2008). Small halogenated urea compounds such as DCIBzL and the nearly isosteric DCFPyL, which were designed to interact with this hydrophobic pocket have very high affinity for PSMA. Chen et al., Clin Cancer Res; 17(24):7645-7653 (2011). Work by Low and co-workers indicated that a thin aminooctanoic acid linker with two phenylalanine residues that interact with a hydrophobic pocket at the mouth of the substrate tunnel is correlated with improved binding. Kularatne et al., Mol Pharm; 6(3):790-800 (2009). Zhang et al. discovered an arene binding site near the entrance to the substrate tunnel that can be used for constructing high affinity ligands. Zhang et al., J Am Chem Soc; 132(36):12711-12716 (2010). More recently, Eder et al. reported a high affinity PSMA targeting tracer with a lipophilic acyclic Ga(III) chelator N,N'-bis [2-hydroxy-5-(carboxyethyl)benzyl] ethylenediamine-N,N'-diacetic acid (HBED-CC). Like many groups working on PSMA tracers, the inventors were focused on binding affinity and the high affinity of RBI-1033 to PSMA was especially attractive. Prior efforts to create a radiolabeled tracer based on RBI-1033 were not successful. The inventors then worked on transforming the 2-5 Å ligand into a peptide equivalent. They generated tri-glutamate (compound 1) and tri-tyrosine (compound 2) mimics of RBI-1033. Neither compound came close to matching the affinity of RBI-1033 which exhibits 10 times better affinity than its parent ligand ZJ24. Cramer et al., Nucleosides Nucleotides Nucleic Acids; 26(10-12):1471-1477 (2007).

Although the affinity of Compounds 1 and 2 do not match that of RBI-1033, the fact that one can place multiple negative charges on the linker without significant reduction in affinity points to a novel engineering pathway for PSMA tracers. Tornachev et al. employed negative charges in a molecule to reduce liver background of Affibody type of molecules. Tolmachev et al., Bioconjug Chem; 21(11):2013-2022 (2010). Affibody molecules are relatively large 7 kD polypeptides where the surface electrostatics of few amino acids may be manipulated without impacting affinity to targets. The effect of charge placement was less certain in a small molecule. The inventors were thus satisfied with the affinity of Compound 1. They proceeded to attach radiolabels to the negatively charged framework. The initial biodistribution study with $^{99m}$Tc labeling and a Gly-Gly-Cys N3S1 chelate indicated significant background due to pertechnetate contamination and the need for a radiochemically pure preparation. After redesigning and radiolabeling the molecule with aluminum-fluoride-NOTA complexes, they were able to demonstrate that this highly negatively charged tracer shows substantially reduced background compared to published values for existing tracers. The liver background of [Al$^{18}$F]5 is 0.17% ID/g at 2 hours compared to 2.17% ID/g for $^{123}$I-MIP-1072, and 2.1% for $^{18}$F-DCFBC and $^{18}$F-DCFPyL. Chen et al., Clin Cancer Res 17(24): 7645-7653 (2011). Blood pool activity 2 hours post injection is 0.04% ID/g for [Al$^{18}$F]5 compared to 0.4% ID/g for $^{18}$FDCFBC and $^{18}$FDCFPyL and 0.21% ID/g for $^{123}$I-MIP-1072. The background in spleen, muscle and bone are very low as well. In fact, [Al$^{18}$F]5 is the only molecule among published PSMA targeting tracers for PET with consistently low background in all major organs except kidney and bladder.

Thus, it appears that high affinity was traded for better background clearance. Such a trade-off is possible because of the unique qualities of PSMA. PSMA has evolved to catalyze the cleavage of peptides containing c-terminal glutamate, so the tunnel is very receptive to negatively charged molecules. This unique property of PSMA allows one to design highly negatively charged substrates with adequate affinity.

It is possible that the fast background clearance is due to negative charges on the NOTA chelate, which contains three carboxylic acid moieties. Although the acid group on NOTA contributes to the overall hydrophilicity, the chelate itself cannot explain rapid background clearance. In comparison with published tracers with an aluminum-fluoride-NOTA complex, [Al$^{18}$F]5 has low background as well. For example, Lang et. al. reported that alpha-v-beta-3 integrin targeting [$^{18}$F]FAl-NOTA-PRGD2 has liver uptake of 1.28±0.28% ID/g at 2 hours and muscle uptake of 0.68±0.06% ID/g at 2 hours. Lang et al., Bioconjug Chem; 22(12):2415-2422 (2011). This is well above the liver level of 0.17±0.03% ID/g and muscle level of 0.01% ID/g for [Al$^{18}$F]5. Laverman et. al. developed a somatostatin receptor targeting $^{18}$F-IMP466 which has blood levels of 0.10±0.07% ID/g and a bone level of 0.33±0.07% ID/g at 2 hours post injection. Laverman et al., Tumour Biol; 33(2): 427-434 (2012). These levels are above the blood level of 0.04±0.01% ID/g and bone level of 0.10±0.02% ID/g for [Al$^{18}$F]5 at 2 hours post injection.

Tumor uptake vs. background: The tumor uptake amounts of [Al$^{18}$F]5 and [$^{99m}$Tc]3 are comparable to other published $^{68}$Ga and $^{99m}$Tc labeled PSMA tracers. Banerjee et al., J Med Chem; 53(14):5333-5341 (2010). The uptake is not as high as that of slightly hydrophobic tracers such as $^{18}$FDCFPyL nor $^{123}$I-MIP-1072. Hillier et al., Cancer Res; 69(17):6932-6940 (2009). This could be because $^{18}$FDCFPyL and $^{123}$I-MIP-1072 have higher affinity to PSMA compared to the highly negatively charged tracers presented in this paper. Another, possibly more important, contributing factor could be the fact that most of the injected tracer molecules are excreted by the kidney before they can make contact with the tumor. Because the tracer is rapidly excreted, lower tumor uptake resulted, but this also improved background clearance. [Al$^{18}$F]5 has the highest tumor to background ratios among published tracers at 2 hours post injection (tumor/blood=115, tumor/liver=27 and tumor/spleen=46, tumor/bone=46 and tumor/muscle=458). This rapid excretion makes the tracer optimal for positron emission tomography with short-lived radionuclides such as $^{18}$F and $^{68}$Ga because of limited time available for background clearance.

Another possible application for these rapidly excreted PSMA-targeting tracers would be for imaging tumor angiogenesis. PSMA is over-expressed in the lumen of tumor neovasculature. Unlike the PSMA expressed on tumor cells, which is located in the interstitial space, the PSMA in tumor vasculature is within the intravascular space. A tracer injected intravenously would have direct and rapid access to the intravascular binding sites. There would be no need for the tracer to diffuse from the intravascular to the interstitial space. The determining factor for the target/background ratio would be background clearance. Rapid background clearance was the guiding principle for the development of glycosylated RGD containing peptides for imaging the alpha-v-beta-3 integrin expression associated with angiogenesis. Haubner et al., J Nucl Med; 42(2):326-336 (2001). $^{18}$F-Galacto-RGD, one of the best studied RGD based agents, demonstrated background levels of 0.30±0.20% ID/g in blood and 2.23±1.02% ID/g in liver at 90 minutes post injection in mice. Pohle et al., Nuclear medicine and biology; 39(6):777-784 (2012). $^{68}$Ga-NODAGA-RGD, a Galacto-RGD derivative with improved elimination kinetics, has background levels of 0.09±0.03% ID/g in blood and 1.58±0.19% ID/g in liver. In comparison, [Al$^{18}$F]5 had background levels of 0.04±0.01% ID/g in blood and 0.17±0.03% ID/g in the liver at 120 minutes. The preliminary 1 hour data for [Al$^{18}$F]5 also showed low background levels with approximately 0.18% ID/g in the blood and 0.4% in the liver. [Al$^{18}$F]5 may have better elimination kinetics than $^{18}$F-Galacto-RGD. Combined with the fact that there is more restricted expression of PSMA in tumors and vasculature relative to alpha-v-beta-3, [Al$^{18}$F]5 could potentially be a better agent for quantifying tumor angiogenesis.

The study described herein is limited by the number of animals in the biodistribution study. Two PC3-PIP tumors were used per mouse to get better tumor uptake statistics with the limited number of mice. The inventors intend to perform a more extensive biodistribution study of [Al$^{18}$F]5 with more mice and with both PC3-PIP (PSMA+) and PC3-flu (PSMA−) tumors in the same mouse. The inventors focused their preliminary biodistribution study on comparing tumor tissues which express PSMA and normal (non-PSMA-expressing) tissues. Having both PIP and flu tumors in the same mouse will allow quantitative comparison of uptake between the PSMA+ and the PSMA− tumors.

Conclusion:

The inventors have demonstrated that PSMA tracers can be designed with a highly negatively charged linker. They found that such molecules are rapidly excreted through the kidneys and show minimal nonspecific binding. The biodistribution properties of [Al$^{18}$F]5 suggest that it has great potential for use with positron emission tomography to image PSMA expressing prostate cancer as well as PSMA expressed in tumor vasculature.

Example 2: Robotic Real-Time Near Infrared Targeted Fluorescence Imaging in a Murine Model of Prostate Cancer The use of near-infrared (NIR) fluorescence is a promising approach for biomedical imaging in living tissue. NIR fluorescence (700-1000 nm) detection avoids the natural background fluorescence interference of biomolecules, providing a high contrast between target and background tissues. Recently, the Food and Drug Administration (FDA) approved for marketing the Intuitive Surgical da Vinci Fluorescence Imaging Vision System, an integration of the SPY imaging technology (Novadaq Technologies, Mississauga, ON, Canada) into the 3-D high-definition imaging capabilities of the da Vinci Surgical Robotic System.

Use of the scope in urology has so far been limited to renal surgery, as kidney fluorescence is intense after intravenous administration of a nontargeted agent such as indocyanine green. Conversely, the prostate does not fluoresce after intravenous administration of a nontargeted agent, and therefore the fluorophore must be modified to specifically bind the prostate.

Prostate-specific membrane antigen (PSMA) is a cell surface glycoprotein with a molecular weight of approximately 100 kDa. It is not expressed in significant amounts in the prostates of mice, dogs, or monkeys. PSMA is expressed in high levels in the human prostate, especially in prostate cancer cells and in the vasculature of primary and metastatic prostate tumors.

In this study, the real-time detection of NIR fluorescence emitted by a PSMA-targeted agent was evaluated using the Intuitive da Vinci Fluorescence Imaging Vision System.

Material and Methods

PSMA Ligand

Figure 4:
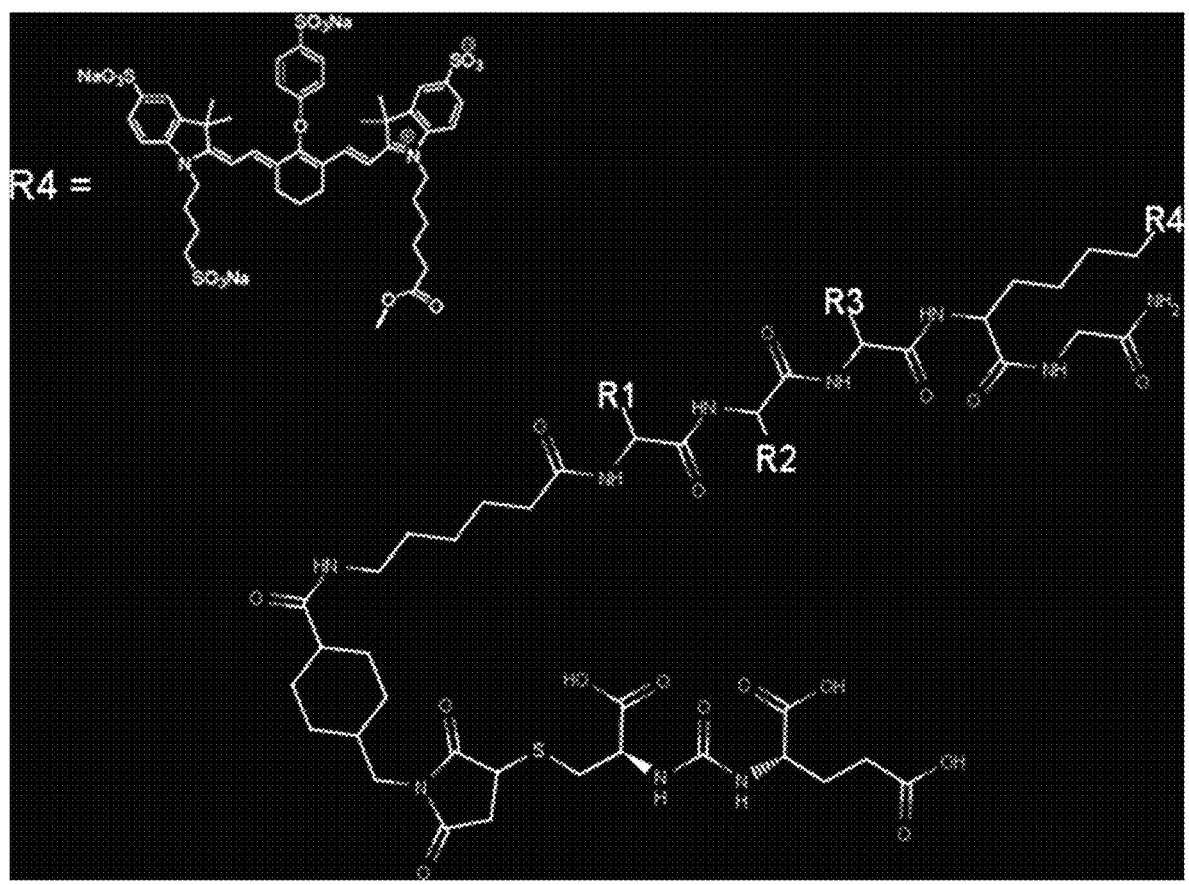
FIG. 4 provides a general schematic representation of the elongated PSMA binding tracers. For ZJ-MCCdEdEdEGK (IRDye800cw)G (SEQ ID NO: 6), R1, R2, and R3 are D-glutamic acid residues; IRDye800cw is attached at the R4 position.

The PSMA targeting ligand ZJ-MCC-dEdEdEGK(IRDye800cw)G (SEQ ID NO: 6) is synthesized using well-established fluorenylmethyloxycarbonyl (FMOC) solid-phase peptide synthesis chemistry. Using a rink-amide or equivalent resin, peptide synthesis started with a stem containing the DGlu-DGlu-DGlu-Gly-Lys-Gly sequence (SEQ ID NO: 24). At the N-terminal end of the stem, the linker succinimidyl-4-(Nmaleimidomethyl) cyclohexane-1-carboxylate [SMCC], Thermo Scientific) was added. Then a glutamate and cysteine containing urea compound (R)-Cys-C(O)—(S)-Glu was added. Kozikowski et al., J Med Chem.; 44:298-301 (2001). After coupling, the entire compound was then cleaved from the solid phase, deprotected with 95% trifluoroacetic acid and purified. An activated ester of IRDye800cw (Li-Cor-*BioScience*, Lincoln, Nebr.), was then reacted with the primary amine on the lysine to create the final tracer (FIG. 4). The final product was purified by high-performance liquid chromatography (HPLC) and reconstituted in 0.2 mL of phosphate-buffered saline, pH 7.

Injection of PSMA-Ligand and Preoperative NIR Imaging

PC3-pip (PSMA-positive) and PC3-flu (PSMA-negative) cells were injected subcutaneously $1.0 \times 10^6$ PC3 cells with 200 □L of matrigel into each flank of 6 NOD SCID Gamma (NSG) mice. Chang et al., Cancer Res.; 59:3192-3198 (1999). After the tumors reached a size of ~5 mm, the mice were anesthetized with isoflurane and were administered 2 or 10 nmol of PSMA-binding fluorescent conjugate via tail vein injection. Preoperative NIR imaging was performed using the Maestro in vivo imaging system (Cambridge Research and Instrumentation, Hopkinton, Mass.). The mice were imaged immediately and at 1-hour intervals after injection of the PSMA targeting fluorescent compound for up to 4 hours. The mice were killed once PSMA+ and PSMA− tumors could be visually differentiated by NIR imaging. The method used was $CO_2$ asphyxiation followed by cervical dislocation.

NIR Fluorescence-Guided Robotic Surgery

Mouse carcasses were operated on using a da Vinci Si Robot (Intuitive Surgical, Sunnyvale, Calif.). A portable dark box was used to minimize ambient light and to allow optimal fluorescence detection. Three robotic instruments (the novel endoscope to detect NIR fluorescence, a scissor, and a grasper) were inserted through robotic trocars positioned across the top cover of the dark box. The tumors were excised using the new robotic camera to detect the fluorescence of the PSMA-binding conjugate. All procedures were done by a single surgeon (R.S.), who had extensive experience in robotic surgery. Tumor specimens were sent for histopathological analysis to assess margin status.

Results

Figure 5:
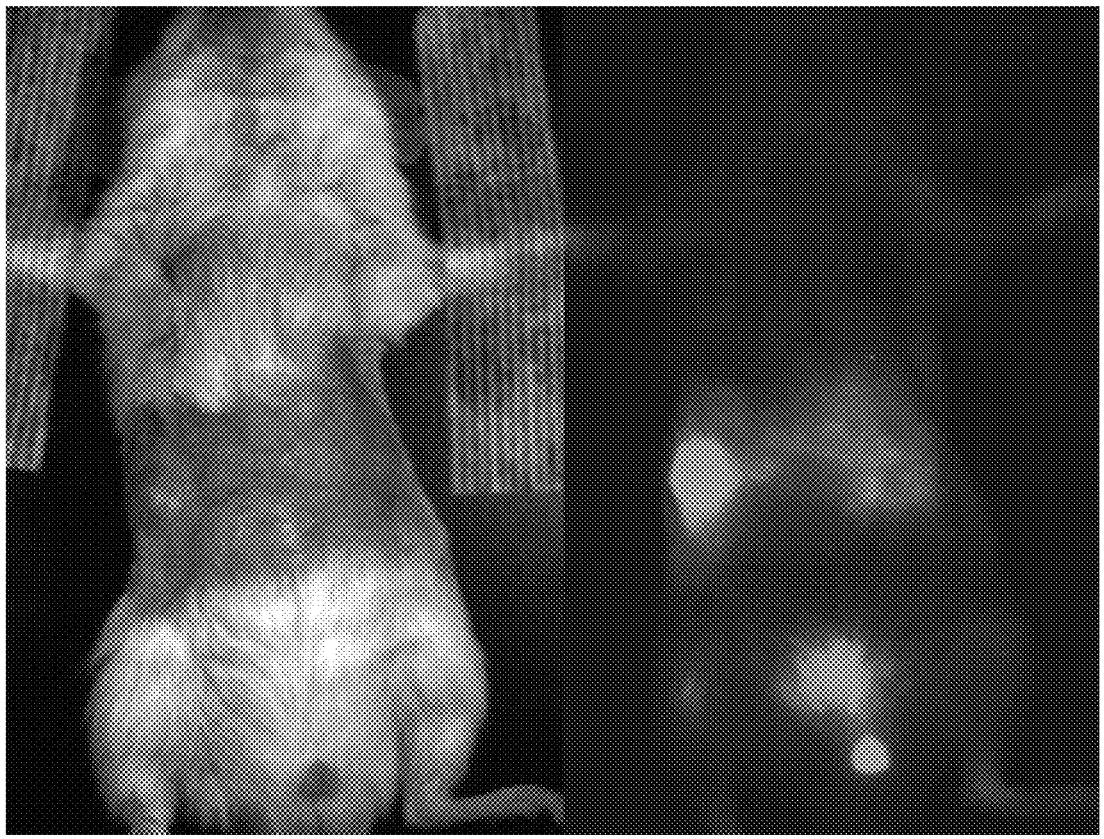
FIG. 5 shows preoperative white light (A) and near-infrared (NIR) fluorescence (B) imaging with the Maestro in vivo imaging system. Note the strong fluorescence signal from the tracer in the right flank (PSMA positive tumor), bladder, and urethra, and the background fluorescence signal from the kidneys. Arrows indicate bulging of the tumor in the skin.

All mice were male, with an average weight of 22 g and a mean age of 49 days by the time that they were killed. The mean size of the tumors was 5.4 mm. In the first 3 mice, 120 minutes was identified as the time to detect peak fluorescence from the PSMA-positive tumors with the Maestro imaging system (FIG. 5). Within 240 minutes, the signal intensity from the tumor was already partially decreased. Based on this information, the last 3 mice were killed at 120 minutes after injection of the conjugate and immediately underwent robotic surgery. Two of the 3 mice injected with 10 nmol of fluorescent compound demonstrated proper targeting on presurgical NIR imaging, whereas the third mouse demonstrated minimal targeting.

Figure 6:
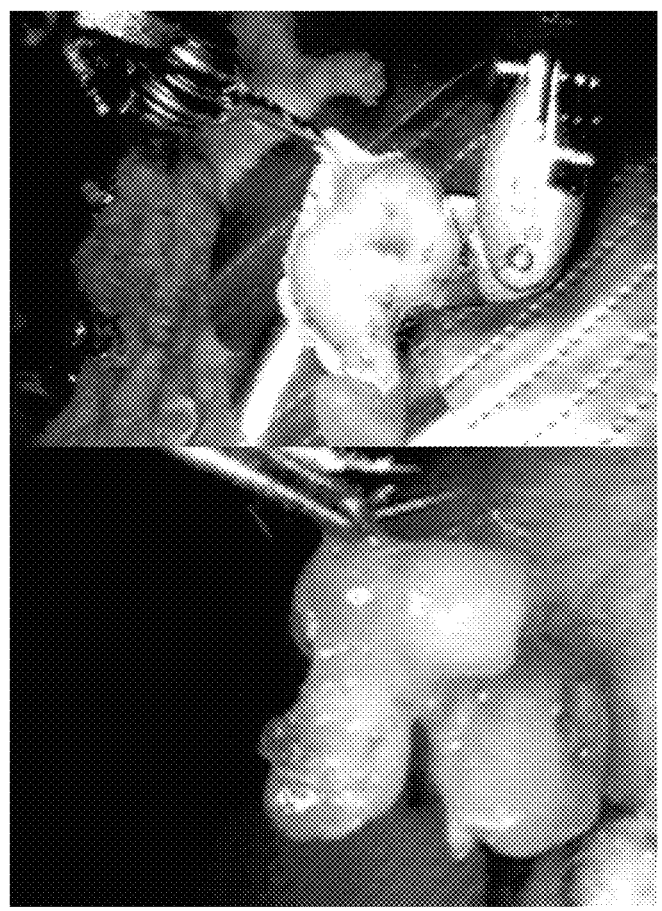
FIG. 6 provides intraoperative images of prostate tumors excised from mice using the da Vinci Si system with a fluorescence detecting endoscope. (A) Fluorescent staining of a PSMA-positive tumor implant using a PSMA binding, fluorescently tagged compound (arrows). (B) Nonstaining of a PSMA negative (control) tumor implant.

During robotic surgery, the inventors were able to detect fluorescence from the PSMA positive tumors in 2 of 3 mice that were injected with 10 nmol of fluorescent compound. However, the intensity of fluorescence was weak (FIG. 6). NIR fluorescence in the base of PSMA positive or PSMA negative tumors was not observed. In the PSMA negative (control) tumors, no tumor fluorescence was identified in any of the mice. In the subcutaneous tissue, the fluorescence was limited to the PSMA positive tumors, and a loss of contrast with surrounding tissues was not observed. Because of the compound's biodistribution and clearance, fluorescence from internal organs (liver, kidneys, and bladder) could also be observed, even without penetrating the abdominal wall musculature, but it did not impair the visualization of the subcutaneous tumor. Given the poor biodistribution of the described fluorescent marker in tissues not directly targeted, loss of contrast compared with surrounding tissues is possible, yet unlikely, with higher concentrations of administered conjugate. Nevertheless, further evaluation is needed to test this hypothesis.

PSMA-positive and -negative tumors had the same gross appearance, except for detectable fluorescence in two of the PSMA positive tumors. No microscopic analysis was performed during resection. Microscopy was obtained later at histopathologic examination, and no fluorescence imaging was performed at that time. The microscopic appearance of PSMA-positive and -negative tumors was indistinguishable. Pathologic examination confirmed prostate cancer and identified negative margins in all 3 PSMA-positive tumors. One of the PSMA-negative tumors had a positive margin.

Comment

The inventors were able to detect NIR fluorescence from prostate cancer implanted in mice with 2 different imaging systems after the intravenous injection of a new compound targeted to PSMA. The prostate tumors were then resected using the Da Vinci Si robot equipped with the Fluorescence Imaging Vision System, and tumor fluorescence was noted in 2 of 3 mice. This is the first description of fluorescence detection from prostate cancer stained with a PSMA-targeted agent by an imaging system developed for minimally invasive surgery.

The real-time intraoperative enhanced visualization of organs and tissues with NIR fluorescent dyes has enormous potential clinical applications, and one of its most promising uses is in oncology. Few NIR fluorophores, such as indocyanine green (ICG) and methylene blue (MB), are approved by the FDA and available for clinical use. In vivo optical imaging probes aiming to identify prostatic tissue intraoperatively are under intense investigation by several groups. PSMA is a potential target for both imaging and treatment purposes. Chen et al synthesized YC-27, also a PSMA-based imaging agent and conjugated it to IRDye 800CW. Chen et al., Biochem Biophys Res Commun.; 390:624-629 (2009). Eifler et al identified in vitro and in vivo NIR fluorescence imaging of LNCaP and PC3-PIP cells using the Fluobeam (Fluoptics, Grenoble, France), which can be used to detect NIR fluorescence during open surgery. Eifler et al., J Urol.; 185:e650-e651 (2011). Liu et al developed Cy5.5-CTT-54.2, another PSMA-targeted NIR fluorescent imaging probe, and identified in vitro NIR fluorescence of LNCaP cells. Liu et al. Bioorg Med Chem Lett.; 20:7124-7126 (2010). Recently, Nakajima et al synthesized a PSMA-targeted activatable monoclonal antibody fluorophore conjugate (J591-ICG) and detected both in vitro and in vivo fluorescence of PC3-PIP cells. Nakajima et al., Bioconjug Chem.; 22:1700-1705 (2011). These new imaging probes, as well as the inventors' conjugate, should undergo toxicity studies before initiating clinical investigation.

Gordetsky et al investigated the use of NIR fluorescence lymph node imaging with open surgery in 14 patients with bladder cancer, using ICG injected at the tumor base. Gordetsky et al., J Urol.; 185:e308-e309 (2011). They used the SPY imaging system (Novadaq Technologies, Mississauga, ON, Canada) to detect fluorescence in pelvic lymph node specimens after 2-4 hours. They were able to identify from 1 to 14 lymph nodes per patient in more than 85% of the patients. One lymph node was positive for high-grade urothelial carcinoma. Van der Poel et al reported the use of a hybrid multimodal radiocolloid (ICG-99mTc-NanoColl) that is both radioactive and fluorescent. van der Poel et al., Eur Urol.; 60:826-833 (2011). After preoperative intraprostatic injection of the tracer under transrectal ultrasound guidance and removal of the prostate, they dissected the sentinel lymph nodes guided by a laparoscopic gamma probe (Europrobe, London, UK) and a fluorescence laparoscope (Karl Storz, Tuttlingen, Germany), being able to link preoperative single-photon emission computed tomography/ computed tomography (SPECT/CT) guidance with intraoperative NIR fluorescence laparoscopy.

Several NIR fluorescent dyes have been developed, with properties that enable them to be conjugated to ligands or monoclonal antibodies directed to certain targets, producing agents molecularly specific to detect cancer cells. The increased tumor angiogenesis and expression of growth signaling receptors are key features that can be used to identify optimal targets. IRDye 800CW, Cy7, and Alexa Fluor 750 are some of the most commonly used fluorophores. The excitation and emission maxima of the IRDye 800CW are centered at 800 nm, which is the optimal wavelength for in vivo imaging, with minimal tissue absorption, autofluorescence, and scattering, yielding excellent signal to background ratios (SBR). Kovar et al., Anal Biochem.; 367:1-12 (2007). IRDye 800CW is highly water soluble and shows very low nonspecific binding to cellular components. Because of their biodistribution and clearance, most fluorescent agents have a high background signal in the kidneys, bladder, and liver. Keereweer et al., Mol Imaging Biol.; 13:199-207 (2011). This was observed in the experiment.

Marshall et al reported no pathologic evidence of toxicity of IRDye 800CW based on hematological, biochemistry, and histopathological analyses. Marshall et al., Mol Imaging Biol.; 12:583-594 (2010). However, linking the fluorescent dye and the targeting moiety produces a new molecule that may have properties different from its original precursors. Thus, NIR contrast agents should undergo toxicity studies of the dye, the targeting ligand, and the final molecule before considering clinical application.

For open surgery, some of the NIR camera systems developed for image-guided procedures are the SPY imaging system (Novadaq Technologies, Mississauga, ON, Canada), the Photodynamic Eye (Hamamatsu Photonics, Hamamatsu City, Japan), the Fluobeam (Fluoptics, Grenoble, France), and the Fluorescence-assisted Resection and Exploration (FLARE) and the Mini-FLARE (Fragioni Laboratory, Brookline, Mass.). In 2011, Intuitive Surgical received FDA approval to market the da Vinci Fluorescence Imaging Vision System. Tobis et al evaluated the new system in 11 patients who underwent robotassisted laparoscopic partial nephrectomy (RALP), using intravenous ICG as the NIR fluorophore. Tobis et al., J Urol.; 186:47-52 (2011). Of the 10 malignant tumors, 70% were hypofluorescent and 30% were isofluorescent in comparison with the normal parenchyma. The vascular anatomy was accurately delineated in all cases with this imaging method.

Fluorescence of organs, such as kidney and liver are straightforward, as nonspecific NIR fluorophores are significantly taken up by these tissues during normal clearance. The prostate, by contrast, does not retain a significant amount of nonspecific fluorescent probe, and therefore intraoperative fluorescence guidance is not possible. The inventors thus sought to develop a targeted fluorophore conjugate that would specifically bind prostatic tissue and lead to detectable levels of fluorescence.

The use of implanted tumors derived from prostate cancer cell lines was chosen, as animals do not express significant levels of PSMA in the prostate. The inventors operated on mouse carcasses instead of live animals, as they were able to observe NIR fluorescence with the Maestro system up to 48 hours after euthanasia in a previous study.

Although NIR fluorescence from prostate tumors was detected with both the Maestro in vivo imaging system and the new robotic scope, the fluorescent signal was considerably less with the robotic system. The fluorescence of the tumor noted by the robotic system was diffuse but with some patchy distribution. Because of the lack of more intense fluorescent staining, it is difficult to completely characterize the staining pattern of individual tissue components. With more intense staining, a complete assessment of the staining pattern should be performed. Several factors could possibly explain the decreased fluorescent signal noted with the robotic system. The camera of the Maestro system can be selected to receive longer periods of exposure to NIR fluorescence, which permits stronger signal detection but is not ideal for real-time image guidance. By contrast, the frame rate of the robotic scope is 30 frames per second, which was adequate for real-time detection of NIR fluorescence from other organs such as the kidney, but may not be optimal to detect fluorescence from prostate tissue with the inventors' tracer. Another possible explanation is that the concentration of 10 nmol, used in the experiments, may not be enough for strong real-time NIR fluorescence detection in prostatic tissue. One also cannot exclude the possibility that a certain amount of the tracer did not reach the intravascular space during the tail vein injection, which could have led to less accumulation in the tumor, impairing its visualization.

Another limitation is the small sample size. However, this was mainly a proof-of-concept study, as it was the first time that the robotic scope was used to detect fluorescence from the PSMA-targeted conjugate.

Even without detecting fluorescence intensity as strong as that seen in the kidneys and bladder, the preliminary results are encouraging. Further studies will be useful to more precisely define the role of NIR fluorescence image-guided robotic surgery, identifying which procedures will be the most suitable for its application. The cause for the positive margins in 1 tumor cannot be precisely determined. Although evidence from this study is not intended or adequate to draw conclusions regarding the improvement of margin status, with further refinement of fluorescent visualization, the precision of tumor resection could potentially increase, minimizing damage to normal tissue and ideally improving tumor margin assessment intraoperatively. Intraoperative robotic fluorescence detection in real time with nonspecific fluorophores, such as ICG, is readily available for clinical use. In the future, other fluorescent dyes suitable for binding to ligands that can be targeted to specific molecules may also obtain approval for clinical use, broadening the spectrum of procedures which can be enhanced by NIR fluorescence-guided surgery.

CONCLUSIONS

This example demonstrates the feasibility of prostatic tissue identification and resection by using a novel robotic fluorescence imaging system in a murine model after the intravenous injection of a PSMA-targeted agent. Further research is warranted to improve real-time fluorescence detection of prostatic tissue and to move this technology toward its potential clinical application.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A PSMA-specific imaging agent comprising a compound according to formula I:

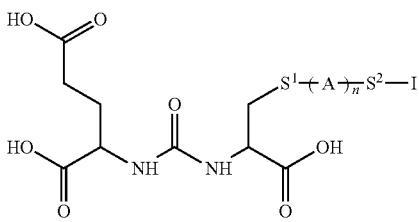

I wherein the agent is selected from the group consisting of E'E-Amc-Ahx-dEdEdEGYGGGC-NH$_2$ (SEQ ID NO: 7), E'E-Amc-Ahx-dEdEdEYK(Bn-NOTA)-NH$_2$ (SEQ ID NO: 8), and E'E-Ahx-EEEYK(Bn-NOTA)-NH$_2$ (SEQ ID NO: 9), and pharmaceutically acceptable salt thereof.

2. A method for imaging prostrate cancer in a tissue region of a subject comprising:

(a) administering to the subject a detectably effective amount of the PSMA-specific imaging agent of claim 1;
(b) allowing a sufficient amount of time for the PSMA-specific imaging agent to enter the tissue region; and
(c) performing imaging of the tissue region of the subject using an imaging device capable of detecting the imaging group.

3. The method of claim 2, wherein the tissue region is the prostate gland.

4. The method of claim 2, further comprising the step of conducting surgery to remove prostate cancer from the subject.

5. The method of claim 4, wherein the surgery is near-infrared fluorescence-guided robotic surgery.

6. The PSMA-specific imaging agent according to claim 1, wherein the agent is E'E-Amc-Ahx-dEdEdEGYGGGC-NH$_2$ (SEQ ID NO: 7).

7. The PSMA-specific imaging agent according to claim 1, wherein the agent is E'E-Amc-Ahx-dEdEdEYK(Bn-NOTA)-NH$_2$ (SEQ ID NO: 8).

8. The PSMA-specific imaging agent according to claim 1, wherein the agent is E'E-Ahx-EEEYK(Bn-NOTA)-NH$_2$ (SEQ ID NO: 9).

* * * * *